US006979338B1

(12) United States Patent
Loshakove et al.

(10) Patent No.: US 6,979,338 B1
(45) Date of Patent: Dec. 27, 2005

(54) LOW PROFILE ANASTOMOSIS CONNECTOR

(75) Inventors: Amir Loshakove, Moshav-Bazra (IL); Ido Kilemnik, Herzelia (IL); Dvir Keren, Petach-Tikva (IL); Nachman Zimet, Tel-Aviv (IL)

(73) Assignee: By-Pass Inc., Orangeburg, NY (US)

( * ) Notice: Subject to any disclaimer, the term of this patent is extended or adjusted under 35 U.S.C. 154(b) by 0 days.

(21) Appl. No.: 09/936,805

(22) PCT Filed: Mar. 20, 2000

(86) PCT No.: PCT/IB00/00310

§ 371 (c)(1),
(2), (4) Date: Sep. 17, 2001

(87) PCT Pub. No.: WO00/56228

PCT Pub. Date: Sep. 28, 2000

Related U.S. Application Data

(63) Continuation-in-part of application No. 09/936,789, filed as application No. PCT/IL99/00674 on Dec. 9, 1999, which is a continuation-in-part of application No. 09/936,806, filed as application No. PCT/IL99/00670 on Dec. 8, 1999, which is a continuation-in-part of application No. 09/701,531, filed as application No. PCT/IL99/00284 on May 30, 1999, application No. 09/936,805, which is a continuation-in-part of application No. 09/701,523, filed as application No. PCT/IL99/00285 on May 30, 1999.

(30) Foreign Application Priority Data

May 29, 1998 (IL) ........................................ 124694
Mar. 19, 1999 (IL) ........................................ 129067

(51) Int. Cl.$^7$ ........................ A61B 17/08; A61B 17/04; A61B 17/34
(52) U.S. Cl. ........................ 606/153; 606/149; 606/185
(58) Field of Search ................................ 606/149, 153, 606/216, 167, 170, 185, 184

(56) References Cited

U.S. PATENT DOCUMENTS

| 1,867,624 A | 7/1932 | Hoffman |
| 2,505,358 A | 4/1950 | Gusberg et al. |
| 2,994,321 A | 8/1961 | Tischler |
| 3,104,666 A | 9/1963 | Hale et al. |
| 3,180,337 A | 4/1965 | Smialowski |
| 3,221,746 A | 12/1965 | Noble |
| 3,519,187 A | 7/1970 | Kapitanov et al. |
| 3,586,002 A | 6/1971 | Wood |

(Continued)

FOREIGN PATENT DOCUMENTS

DE 28 22 603 11/1979

(Continued)

OTHER PUBLICATIONS

Certified Copy of U.S. Appl. No. 09/324,997,published on Sep. 14, 2000, Grudem,J. et al., "Medical Grafting Methods and Apparatus".

(Continued)

Primary Examiner—Cary E. O'Connor
(74) Attorney, Agent, or Firm—Fenster & Company

(57) ABSTRACT

An anastomosis connector comprises a plurality of ring segments (106), together defining a radially expandable ring-like shape (106) having a lumen; at least one pivot bar (114) coupled to at least one of said ring segments (106); at least one spike (109) mounted on said pivot bar (114) and rotatable around said pivot bar (114), wherein radial deformation of said ring-like shape (106) does not substantially directly affect said spike (109) rotational position.

73 Claims, 25 Drawing Sheets

U.S. PATENT DOCUMENTS

| | | | |
|---|---|---|---|
| 3,657,744 A | 4/1972 | Ersek | |
| 3,776,237 A | 12/1973 | Hill et al. | |
| 3,825,010 A | 7/1974 | McDonald | |
| 3,837,345 A | 9/1974 | Matar | |
| 3,901,243 A | 8/1975 | Read | |
| 3,908,662 A * | 9/1975 | Razgulov et al. | |
| 3,973,570 A | 8/1976 | Razgulov et al. | |
| 4,018,228 A | 4/1977 | Goosen | |
| 4,069,826 A | 1/1978 | Sessions et al. | |
| 4,214,586 A | 7/1980 | Mericle | |
| 4,214,587 A | 7/1980 | Sakura, Jr. | |
| 4,216,776 A | 8/1980 | Downie et al. | |
| 4,352,358 A | 10/1982 | Angelchik | |
| 4,366,819 A | 1/1983 | Kaster | |
| 4,368,734 A | 1/1983 | Banko | |
| 4,368,736 A | 1/1983 | Kaster | |
| 4,387,879 A | 6/1983 | Tauschinski | |
| 4,485,816 A | 12/1984 | Krumme | |
| 4,523,592 A | 6/1985 | Daniel | |
| 4,586,503 A | 5/1986 | Kirsch et al. | |
| 4,657,019 A | 4/1987 | Walsh et al. | |
| 4,676,245 A | 6/1987 | Fukuda | |
| 4,696,300 A | 9/1987 | Anderson | |
| 4,696,308 A | 9/1987 | Meller et al. | |
| 4,785,809 A | 11/1988 | Weinrib | |
| 4,796,627 A | 1/1989 | Tucker | |
| 4,846,174 A | 7/1989 | Willard et al. | |
| 4,872,874 A | 10/1989 | Taheri | |
| 4,917,087 A | 4/1990 | Walsh et al. | |
| 4,926,858 A | 5/1990 | Gifford, III et al. | |
| 4,930,502 A | 6/1990 | Chen | 606/150 |
| 4,930,674 A | 6/1990 | Barak | |
| 4,958,414 A | 9/1990 | Benoit | |
| 4,997,439 A | 3/1991 | Chen | 606/216 |
| 5,009,643 A | 4/1991 | Reich et al. | |
| 5,035,702 A | 7/1991 | Taheri | |
| 5,037,433 A | 8/1991 | Wilk et al. | |
| 5,041,082 A | 8/1991 | Shiber | |
| 5,047,047 A | 9/1991 | Yoon | 606/216 |
| 5,129,913 A | 7/1992 | Ruppert | |
| 5,141,516 A | 8/1992 | Detweiler | |
| 5,158,566 A | 10/1992 | Pianetti | 606/216 |
| 5,188,636 A | 2/1993 | Fedotov | |
| 5,192,294 A | 3/1993 | Blake, III | |
| 5,197,465 A | 3/1993 | Montgomery | |
| 5,201,901 A | 4/1993 | Harada et al. | 606/198 |
| 5,222,974 A | 6/1993 | Kensey et al. | |
| 5,234,447 A | 8/1993 | Kaster et al. | |
| 5,234,448 A | 8/1993 | Wholey et al. | |
| 5,236,437 A | 8/1993 | Wilk et al. | |
| 5,250,058 A | 10/1993 | Miller et al. | |
| 5,254,127 A | 10/1993 | Wholey et al. | |
| 5,275,622 A | 1/1994 | Lazarus et al. | |
| 5,282,827 A | 2/1994 | Kensey et al. | 606/215 |
| 5,284,485 A | 2/1994 | Kammerer et al. | |
| 5,292,309 A | 3/1994 | Van Tassel et al. | |
| 5,323,765 A | 6/1994 | Brown | |
| 5,366,462 A | 11/1994 | Kaster et al. | |
| 5,392,979 A | 2/1995 | Green et al. | 227/179 |
| 5,403,333 A | 4/1995 | Kaster et al. | 606/151 |
| 5,403,338 A | 4/1995 | Milo | |
| 5,425,739 A | 6/1995 | Jessen | |
| 5,441,517 A | 8/1995 | Kensey et al. | |
| 5,445,623 A | 8/1995 | Richmond | 604/251 |
| 5,445,632 A | 8/1995 | Blake et al. | |
| 5,456,712 A | 10/1995 | Maginot | 606/153 |
| 5,478,353 A | 12/1995 | Yoon | |
| 5,478,354 A | 12/1995 | Tovey et al. | 606/219 |
| 5,486,187 A | 1/1996 | Schenck | 606/153 |
| 5,488,958 A | 2/1996 | Topel et al. | |
| 5,484,451 A | 6/1996 | Akopov et al. | |
| D372,310 S | 7/1996 | Hartnett | |
| 5,536,251 A | 7/1996 | Evard et al. | |
| 5,540,715 A | 7/1996 | Katsaros et al. | |
| 5,562,690 A | 10/1996 | Green et al. | |
| 5,562,728 A | 10/1996 | Lazarus et al. | |
| 5,575,800 A | 11/1996 | Gordon | |
| 5,591,178 A | 1/1997 | Green et al. | |
| 5,618,311 A | 4/1997 | Gryskiewicz | 606/216 |
| 5,649,946 A | 7/1997 | Bramlet | |
| 5,658,282 A | 8/1997 | Daw et al. | |
| 5,676,670 A | 10/1997 | Kim | |
| 5,676,689 A | 10/1997 | Kensey et al. | 606/213 |
| 5,676,696 A | 10/1997 | Marcade | |
| 5,685,838 A | 11/1997 | Peters et al. | |
| 5,690,656 A | 11/1997 | Cope et al. | |
| 5,690,662 A | 11/1997 | Chiu et al. | |
| 5,695,504 A | 12/1997 | Gifford, III et al. | |
| 5,702,412 A | 12/1997 | Popov et al. | |
| 5,707,380 A | 1/1998 | Hinchliffe et al. | |
| 5,707,393 A | 1/1998 | Kensey et al. | 606/213 |
| 5,709,335 A | 1/1998 | Heck | |
| 5,733,308 A | 3/1998 | Daugherty et al. | 604/164 |
| 5,746,755 A | 5/1998 | Wood et al. | 606/148 |
| 5,755,778 A | 5/1998 | Kleshinski | |
| 5,758,663 A | 6/1998 | Wilk et al. | |
| 5,759,194 A | 6/1998 | Hammerslag | 606/214 |
| 5,779,719 A | 7/1998 | Klein et al. | 606/144 |
| 5,792,173 A | 8/1998 | Breen et al. | 606/201 |
| 5,797,920 A | 8/1998 | Kim | |
| 5,797,933 A | 8/1998 | Snow et al. | 606/157 |
| 5,797,934 A | 8/1998 | Rygaard | |
| 5,814,005 A | 9/1998 | Barra et al. | 604/8 |
| 5,817,111 A | 10/1998 | Riza | |
| 5,817,113 A | 10/1998 | Gifford, III et al. | |
| 5,823,971 A | 10/1998 | Robinson et al. | 600/567 |
| 5,824,002 A | 10/1998 | Gentelia et al. | 604/164 |
| 5,824,008 A | 10/1998 | Bolduc et al. | |
| 5,827,316 A | 10/1998 | Young et al. | |
| 5,830,222 A | 11/1998 | Makower | |
| 5,833,698 A | 11/1998 | Hinchliffe et al. | |
| 5,861,004 A | 1/1999 | Kensey et al. | 606/213 |
| 5,868,763 A | 2/1999 | Spence et al. | |
| 5,893,369 A | 4/1999 | LeMole | |
| 5,910,153 A | 6/1999 | Mayenberger | 606/184 |
| 5,910,155 A | 6/1999 | Ratcliff et al. | |
| 5,922,000 A | 7/1999 | Chodorow | |
| 5,931,842 A | 8/1999 | Goldsteen et al. | |
| 5,935,147 A | 8/1999 | Kensey et al. | 606/213 |
| 5,948,425 A | 9/1999 | Janzen et al. | |
| 5,957,938 A | 9/1999 | Zhu et al. | |
| 5,957,973 A | 9/1999 | Quiachon et al. | |
| 5,964,782 A | 10/1999 | Lafontaine et al. | |
| 5,968,069 A | 10/1999 | Dusbabek et al. | |
| 5,972,014 A | 10/1999 | Nevins | 606/198 |
| 5,976,159 A | 11/1999 | Bolduc et al. | |
| 5,976,178 A | 11/1999 | Goldsteen | |
| 5,989,278 A | 11/1999 | Mueller | |
| 5,989,287 A | 11/1999 | Yang et al. | |
| 5,993,468 A | 11/1999 | Rygaard | |
| 6,004,330 A | 12/1999 | Middleman et al. | |
| 6,004,341 A | 12/1999 | Zhu et al. | |
| 6,022,351 A | 2/2000 | Bremer et al. | |
| 6,022,367 A | 2/2000 | Sherts | 606/184 |
| 6,024,763 A | 2/2000 | Lenker et al. | |
| 6,026,814 A | 2/2000 | LaFontaine et al. | |
| 6,035,856 A | 3/2000 | LaFontaine et al. | |
| 6,036,702 A | 3/2000 | Bachinski et al. | |
| 6,071,292 A | 6/2000 | Makower et al. | |
| 6,080,176 A | 6/2000 | Young | |
| 6,113,612 A | 9/2000 | Swanson et al. | |
| 6,152,937 A * | 11/2000 | Peterson et al. | 606/153 |
| 6,165,185 A | 12/2000 | Shennib et al. | 606/155 |
| 6,171,319 B1 | 1/2001 | Nobles et al. | |

| | | |
|---|---|---|
| 6,176,867 B1 | 1/2001 | Wright |
| 6,179,848 B1 | 1/2001 | Solem |
| 6,185,792 B1 | 2/2001 | Nelson et al. |
| 6,186,942 B1 | 2/2001 | Sullivan et al. |
| 6,190,353 B1 | 2/2001 | Makower et al. |
| 6,193,734 B1 | 2/2001 | Bolduc et al. ............... 606/153 |
| 6,206,912 B1 | 3/2001 | Goldsteen et al. |
| 6,248,117 B1 | 6/2001 | Blatter et al. |
| 6,251,116 B1 | 6/2001 | Shennib et al. ............. 606/155 |
| 6,261,315 B1 | 7/2001 | St. Germain et al. |
| 6,302,905 B1 | 10/2001 | Goldsteen et al. |
| 6,309,416 B1 * | 10/2001 | Swanson et al. ........... 623/1.23 |
| 6,383,208 B1 | 5/2002 | Sancoff et al. ............... 606/213 |
| 6,387,108 B1 | 5/2002 | Taylor et al. |
| 6,391,036 B1 | 5/2002 | Berg et al. |
| 6,391,038 B2 | 5/2002 | Vargas et al. ................ 606/153 |
| 6,398,797 B2 | 6/2002 | Bombard et al. ........... 606/153 |
| 6,402,764 B1 | 6/2002 | Hendricksen et al. ....... 606/149 |
| 6,419,681 B1 | 7/2002 | Vargas et al. ................ 606/153 |
| 6,428,550 B1 | 8/2002 | Vargas et al. |
| 6,461,320 B1 | 10/2002 | Yencho et al. |
| 6,478,804 B2 | 11/2002 | Vargas et al. |
| 6,485,496 B1 | 11/2002 | Suyker et al. ............... 606/153 |
| 6,497,710 B2 | 12/2002 | Yencho et al. |
| 6,508,252 B1 | 1/2003 | Berg et al. |
| 6,514,196 B1 | 2/2003 | Sullivan et al. |
| 6,514,265 B2 | 2/2003 | Ho et al. |
| 6,517,558 B2 | 2/2003 | Gittings et al. |
| 6,533,812 B2 | 3/2003 | Swanson et al. |
| 6,537,287 B1 | 3/2003 | Yencho et al. |
| 6,537,288 B2 | 3/2003 | Vargas et al. |
| 6,588,643 B2 | 7/2003 | Bolduc et al. |
| 6,652,541 B1 | 11/2003 | Vargas et al. |
| 6,659,173 B2 | 12/2003 | Kirk et al. |
| 2001/0004698 A1 | 6/2001 | Blatter et al. |
| 2001/0004699 A1 | 6/2001 | Gittings et al. |
| 2001/0016752 A1 | 8/2001 | Berg et al. |
| 2001/0025643 A1 | 10/2001 | Foley |
| 2001/0047180 A1 * | 11/2001 | Grudem et al. ............. 606/153 |
| 2002/0004663 A1 | 1/2002 | Gittings et al. |
| 2002/0019642 A1 | 2/2002 | Milliman et al. |
| 2002/0022852 A1 | 2/2002 | Dakov |
| 2002/0022857 A1 | 2/2002 | Goldsteen et al. |
| 2002/0058955 A1 | 5/2002 | Blatter et al. |
| 2002/0082614 A1 | 6/2002 | Logan et al. |
| 2002/0087046 A1 | 7/2002 | Sullivan et al. |
| 2002/0087181 A1 | 7/2002 | Goldsteen et al. |
| 2002/0091398 A1 | 7/2002 | Galdonik et al. |
| 2002/0099394 A1 | 7/2002 | Houser et al. |
| 2002/0108621 A1 | 8/2002 | Berg et al. |
| 2002/0169470 A1 | 11/2002 | Kuhr et al. |
| 2003/0083541 A1 | 5/2003 | Sullivan et al. |
| 2003/0083679 A1 | 5/2003 | Grudem et al. |
| 2003/0093118 A1 | 5/2003 | Ho et al. |

FOREIGN PATENT DOCUMENTS

| | | |
|---|---|---|
| DE | 31 47 609 | 6/1983 |
| DE | 297 13 335 | 11/1997 |
| EP | 0 539 237 | 4/1993 |
| EP | 0 774 237 | 5/1997 |
| EP | 0 916 314 | 5/1999 |
| EP | 1 055 401 | 11/2000 |
| GB | 2 094 212 | 9/1982 |
| IT | 1215699 | 2/1990 |
| WO | WO 89/06515 | 7/1989 |
| WO | WO 89/08433 | 9/1989 |
| WO | WO 95/26170 | 10/1995 |
| WO | WO 96/25886 | 8/1996 |
| WO | WO 96/33673 | 10/1996 |
| WO | WO 97/07741 | 3/1997 |
| WO | WO 97/13463 | 4/1997 |
| WO | WO 97/13471 | 4/1997 |
| WO | WO 97/27898 | 8/1997 |
| WO | WO 97/28749 | 8/1997 |
| WO | WO 97/40754 | 11/1997 |
| WO | WO 98/07399 | 2/1998 |
| WO | WO 98/16161 | 4/1998 |
| WO | WO 98/19629 | 5/1998 |
| WO | WO 98/19634 | 5/1998 |
| WO | WO 98/19635 | 5/1998 |
| WO | WO 98/19636 | 5/1998 |
| WO | WO 98/30152 | 7/1998 |
| WO | WO 98/32412 | 7/1998 |
| WO | WO 98/38922 | 9/1998 |
| WO | WO 98/38939 | 9/1998 |
| WO | WO 98/38941 | 9/1998 |
| WO | WO 98/38942 | 9/1998 |
| WO | WO 98/42262 | 10/1998 |
| WO | WO 98/55027 | 12/1998 |
| WO | WO 98/57591 | 12/1998 |
| WO | WO 98/57592 | 12/1998 |
| WO | WO 99/21491 | 5/1999 |
| WO | WO 99/37218 | 7/1999 |
| WO | WO 99/38441 | 8/1999 |
| WO | WO 99/40851 | 8/1999 |
| WO | WO 99/40868 | 8/1999 |
| WO | WO 99/62415 | 12/1999 |
| WO | WO 99/65409 | 12/1999 |
| WO | WO 00/21436 | 4/2000 |
| WO | WO 00/27311 | 5/2000 |
| WO | WO 00/27312 | 5/2000 |
| WO | WO 00/27313 | 5/2000 |
| WO | WO 00/45886 | 8/2000 |
| WO | WO 00/53104 | 9/2000 |
| WO | WO 00/66007 | 11/2000 |
| WO | WO 00/66009 | 11/2000 |
| WO | WO 00/69343 | 11/2000 |
| WO | WO 00/69346 | 11/2000 |
| WO | WO 00/69349 | 11/2000 |
| WO | WO 00/69364 | 11/2000 |
| WO | WO 00/72764 | 12/2000 |
| WO | WO 00/74579 | 12/2000 |
| WO | WO 01/08566 | 2/2001 |
| WO | WO 01/15607 | 3/2001 |
| WO | WO 01/15609 | 3/2001 |
| WO | WO 01/17440 | 3/2001 |
| WO | WO 01/17441 | 3/2001 |
| WO | WO 01/19256 | 3/2001 |
| WO | WO 01/19259 | 3/2001 |
| WO | WO 01/26562 | 4/2001 |
| WO | WO 01/30444 | 5/2001 |
| WO | WO 02/13702 | 2/2002 |

OTHER PUBLICATIONS

Certified Copy of U.S. Appl. No. 60/137,764,published on Dec. 14, 2000, Logan,J. et al., "Mechanical Anastomosis Delivery Apparatus".

Draney,M. et al.; "Coronary Artery Bypass Surgery: Minimally Invasive Techniques";May 1998; Retrieved from Internet:<http://me210abc.stanford.edu/94-95/projects/Pfizer/Spring/l.html>.

Obora, Y. et al.; "Nonsuture Mircovascular Anastomsis Using Magnet Rings: Preliminary Report";Feb. 1978; pp. 117-120; SurNeurol (United States); vol. 9, No. 2.

Östrup, L. T. et al.; "The UNILINKInstrument System for Fast and Safe Microvascular Anastomosis"; pp. 521-526; Department of Plastic Surgery, Hand Surgery, and Burns; University Hospital, Sweden; presented in part at the First Scandinavian Seminar on Reconstructive Microsurgery, Sweden, Oct. 1979, and at the Symposium on MicroncurovascularSurgery, Denmark, Jan. 1983.

Yachia, D. et al.; "Bio-FragmentableAnastomosia Ring in Urological Surgery Involving the GastrointestinalTract: Early Experiences and a Historical Review of Mechanical Intestinal Anastomosis"; May 1995; pp. 1426-1428; The Journal of Urology; vol. 153.

Certified Copy of U.S. Appl. No. 09/187,361, published on May 18, 2000, Galdonik, J. A. et al., "Medical Graft Component and Methods of Installing Same".

Certified Copy of U.S. Appl. No. 09/187,364, published on May 18, 2000, Berg, T. A. et al., "Minimally Invasive RevascularizationApparatus and Methods".

US 6,503,260, 01/2003, Schaller et al. (withdrawn)

* cited by examiner

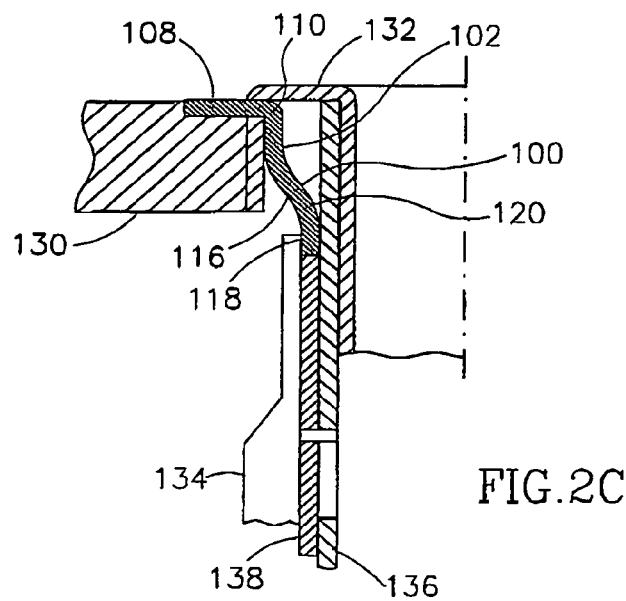
FIG.2C
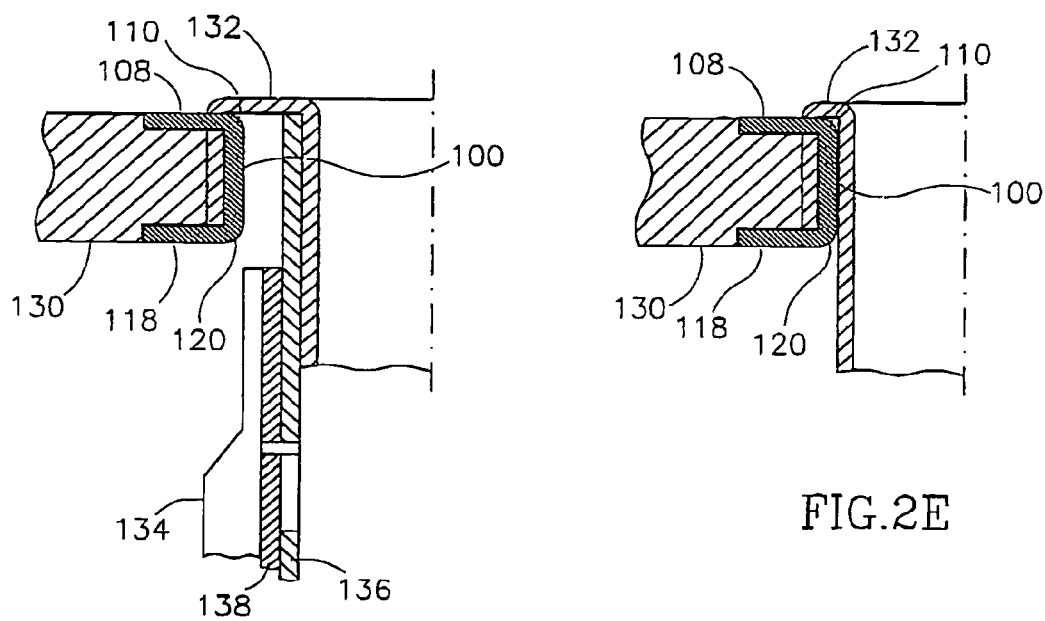
FIG.2D
FIG.2E

LOW PROFILE ANASTOMOSIS CONNECTOR

RELATED APPLICATIONS

The present application is also a continuation-in-part of Ser. No. 09/936,789 filed Sep. 17, 2001, which is a 371 of PCT/IL99/00674 filed Dec. 9, 1999, which is a continuation-in-part of Ser. No. 09/936,806 filed Sep. 17,2001 which is a 371 of PCT/IL99/00670 filed Dec. 8, 1999 which is a continuation-in-part of Ser. No. 09/701,531 filed Nov. 28,2000, which is a 371 of PCT/IL99/00284. The present application is also a continuation-in-part of Ser. No. 09/701,523 filed Nov. 28, 2000 which is a 371 of PCT/IL99/00285, filed May 30, 1999.

FIELD OF THE INVENTION

The present invention relates to anastomosis connectors and especially to anastomosis connectors having a low profile.

BACKGROUND OF THE INVENTION

Various types of anastomosis connectors, for connecting two blood vessels, have been suggested in the art.

One drawback of some connectors is their non-trivial profile, i.e., the connectors project outside of the volume defined by the anastomosis region. As many such connectors are formed of hard materials, these extensions may damage nearby tissue. One cause of these projections has been the use of spikes that are bent during the anastomosis procedure. A bent spike requires a non-trivial bending radius, to prevent spike failure, especially if the spike is elastic, super elastic or shape-memory based. It is noted that elastic, super-elastic and shape-memory bending mechanisms are limited with respect to the amount of elongation that the mechanism can faithfully retain. With plastic deformations, the bending is limited by the danger of mechanical failure. In general, the range of materials (and their mechanical characteristics) available for implantation is quite limited, due to biocompatibility considerations.

U.S. Pat. No. 5,234,447 to Kaster, the disclosure of which is incorporated herein by reference, describes a plastically deformed anastomosis device for a side to end anastomosis between a side vessel and an everted graft. The device comprises a solid ring having a plurality of forward spikes and a plurality of backwards spikes extending axially from the ring. Forward spikes exit through the tip of the everted graft and typically engage the target side vessel from inside. Backward spikes do not need to pierce the graft and engage the target vessel from its outside.

SUMMARY OF THE INVENTION

An aspect of some preferred embodiments of the invention relates to providing a pivot bar on which a spike of an anastomosis device is mounted. In a preferred embodiment of the invention, the pivot bar is not part of the mechanical structure of the connector, allowing the spike to deform independently of the deformation of the rest of the connector, even if the device deformation is not restricted by a mold. In a preferred embodiment of the invention, the pivot bar is used to provide apply sufficient force to the spike, without requiring a significant bending radius. Thus, a device whose profile conforms to the blood vessels being connected, can be provided. Such a pivot bar can be provided for spikes that engage one blood vessel or both blood vessels.

A low profile is useful in a forward spike of the anastomosis connector, for example to reduce tension at the connection and/or reduce blood-connector contact. A low profile is useful in the backward spike of the connector, for example to minimally impact graft flexibility and/or to prevent inadvertent damaging of nearby structures. In some designs, a low profile device may also be more easily provided by flexible means, such as a catheter.

Another potential advantage of a low profile device is that the device does not restrict the motion of the graft relative to the target vessel. Thus, the graft can move, and, especially, the graft can assume a non-perpendicular orientation relative to the vessel. In other embodiments, restriction of the graft motion and/or extension direction may be desired, so an extended connector may be provided.

In a preferred embodiment of the invention, at least some of the pivot bars are not straight, optionally allowing for greater force application at some bending positions of the pivot bars.

In one preferred embodiment of the invention, a spike (mounted on a pivot bar) is cut out of the material from which an opposing spike is formed.

In a preferred embodiment of the invention, a connector comprises a ring with a plurality of radially displaced spikes on pivot bars. Preferably, the pivot bar heights are staggered and/or the pivot bars are angled, allowing a better radial compression of the connector, during insertion of the connector into the side vessel.

An aspect of some preferred embodiments of the invention relates to an anastomosis connector for a side to end anastomosis, in which at least some of the backward (or forward) spikes do not penetrate the "side" vessel. Rather, the spikes press against the vessels and prevent the "end" vessel from advancing too far (or retracting) into the side vessel. Preferably, these pressing spikes are mounted on pivot bars, to allow a large force to be applied, without requiring a significant bend area. Alternatively or additionally, such a pressing spike can be substantially parallel to the surface of the "side" vessel, reducing vessel motion at the connection area and/or allowing a better spreading out of pressure.

An aspect of some preferred embodiments of the invention relates to the design of a ring-part of an anastomosis device. In a preferred embodiment of the invention, the anastomosis device comprises a plurality of ring segments arranged in a ring, with spike elements between the ring segments. In a preferred embodiment of the invention, the ring segments comprises arcs, for example each such ring segment comprising two, three or four parallel arcs interconnecting two neighboring spike elements. Preferably, all the ring segments have their arcs in the same direction, however, this is not required. Alternatively to arcs, a ring segment may comprise one or more zigzag elements, for example including two or more bends. In some embodiments, the arc or zigzag thickness may vary along a single ring segment.

In a preferred embodiment of the invention, a strengthening or a loop is provided at the point of connection between the arc (or other ring segment) and the spike element. The strengthening or the loop serves to distribute strain caused by radially contracting the connector and/or to prevent over-straining at the point of connection.

An aspect of some preferred embodiment of the invention relates to a graft eversion mechanism. In a preferred embodiment of the invention, the eversion mechanism comprises a graft holder and a plurality of forceps like devices. In a preferred embodiment of the invention, the forceps like devices can be operated in tandem, to grasp the ends of the graft, evert it and then pull the everted part back over the rest of the graft. Preferably, the different forceps pull the graft back different amounts, forming an uneven eversion.

An aspect of some preferred embodiments of the invention relates to performing an oblique eversion. In a preferred embodiment of the invention, it is noted that an obliquely everted graft, especially a vein, tends to form an oblique anastomosis connection and the graft tends to bend back to relieve the strain caused by the oblique eversion. Preferably, the degree of obliqueness is selected responsive to an expected bending of the graft after the anastomosis is completed.

An aspect of some preferred embodiments of the invention relates to a method of forming an oblique-connection anastomosis device. In a preferred embodiment of the invention, a perpendicular-connection anastomosis device is formed and then bent out of shape, to provide an oblique device. The bent device is preferably heat treated to train it to its new geometry.

An aspect of some preferred embodiments of the invention relates to an apparatus for delivering a graft to an anastomosis location. In a preferred embodiment of the invention, the apparatus comprises two parts, a handle, and a replaceable inner-tool, which can be, for example, a hole-puncher or a graft delivery and anastomosis performance tool. In a preferred embodiment of the invention, the inner tool is inserted into the handle from the side of the handle. In an exemplary embodiment, the tool is inserted into the side of the handle and than slid axially a short distance to lock. A potential advantage of this method is that a vein can be mounted on the graft delivery tool prior to its being mounted o the handle and there is little danger of the vein being damage by the handle.

An aspect of some preferred embodiments of the invention relates to a punch for punching holes in blood vessels. Such a punch may be used from outside the body, or form inside the body, for example being provided through an endoscope or a catheter. In a preferred embodiment of the invention, the punch comprises a pointed shaft having a circumferential depression with defined therein. At least the end of the depression near the tip is sloping. An outer tube is provided over the shaft. The tip of the tube has a smaller inner diameter than the rest of the tube. In operation, the tip is inserted into a side of a blood vessel until the vessel wall is engaged by the depression. The tube is then advanced. The vessel wall is cut between the inner diameter of the outer tube and the sloping edge of the depression. The cut out portion is preferably contained in the depression.

An aspect of some preferred embodiments of the invention relates to a device for measuring and preferably prestretching a graft before an anastomosis procedure. In a preferred embodiment of the invention, the device comprises two bars, a first one connected to a handle and a second one connected to a weak spring and a scale. The graft is mounted on the two bars. When the handle is pulled, the motion of the first bar is coupled to the second bar via the graft. The motion of the second bar is limited by the spring. The scale shows the relative distance between the two bars, allowing a suitable anastomosis connector to be selected. Further pulling on the handle can be used to pre-stretch the vein in preparation for eversion and/or mounting of the anastomosis connector on it.

There is thus provided in accordance with a preferred embodiment of the invention, an anastomosis connector, comprising:

a plurality of ring segments, together defining a radially expandable ring-like shape having a lumen;

at least one pivot bar coupled to at least one of said ring segments; and at least one spike mounted on said pivot bar and rotatable around said pivot bar, where radial deformation of said ring-like shape does not substantially directly affect said spike rotational position. Preferably, rotation of the pivot bar is mechanically decoupled from radial deformation of ring-like shape. Preferably, said at least one pivot bar comprises at leas two pivot bars, where said at least one spike is mounted on a first one of said pivot bars and said first pivot bar is mounted on the other pivot bar.

In a preferred embodiment of the invention, said at least one spike is pointed towards said ring-like shape. Alternatively, said at least one spike is pointed away from said ring-like shape.

In a preferred embodiment of the invention, said at least one spike comprises at least two spikes, each mounted on a separate pivot bar, where said spikes point in opposite directions along an axis of said connector.

In a preferred embodiment of the invention, said connector is designed such that said at least one spike remains outside of a side vessel in an end-to-side anastomosis. Alternatively or additionally, said connector is designed such that said at least one spike enters a side vessel in an end-to-side anastomosis.

In a preferred embodiment of the invention, said pivot bar is comprised in a spike element. Preferably, said spike element comprises two opposing spikes. Alternatively or additionally, said spike element interconnects two adjacent ring segments. Alternatively, said spike element is attached to only a single ring element.

In a preferred embodiment of the invention, said at least one spike has a tip adapted to penetrate a blood vessel. Alternatively, said at least one spike has a tip adapted to lay against a blood vessel without penetrating it.

In a preferred embodiment of the invention, said connector is heat-treated to have said at least one spike perpendicular to said ring. Alternatively, said connector is heat-treated to have said at least one spike parallel to said ring.

In a preferred embodiment of the invention, said connector is heat-treated to have said at least one spike bend. Alternatively, said connector is heat-treated such that said at least one spike does not bend.

In a preferred embodiment of the invention, said connector is heat-treated such that said pivot bar is twisted. Alternatively, said connector is heat-treated such that said pivot bar is not twisted.

In a preferred embodiment of the invention, said pivot bar is within an axial extent of said ring-like shape. Preferably, said pivot bar is substantially centered relative to said ring like shape.

Alternatively, said pivot bar is outside an axial extent of said ring-like shape.

In a preferred embodiment of the invention, said pivot bar is comprised in a pivot mechanism. Preferably, said pivot mechanism is directly mounted onto at least one of said ring elements. Alternatively, said pivot mechanism is coupled via a single extension to at least one of said ring elements. Alternatively, said pivot mechanism is coupled via at least two extensions to at least one of said ring elements.

In a preferred embodiment of the invention, said pivot bar is coupled to said pivot mechanism via a hinge at each end of said pivot bar. Preferably, said hinge comprises a thickening of said mechanism relative to said pivot bar.

In a preferred embodiment of the invention, said connector comprises a plurality of alternating ring segments and pivot bar mechanism and said pivot bar mechanisms are axially staggered, to allow a greater radial compression of said ring-like shape.

In a preferred embodiment of the invention, said pivot bar is straight. Alternatively, said pivot bar is piece-wise straight. alternatively, said pivot bar is curved.

In a preferred embodiment of the invention, said connector is packaged. Preferably, said packaging indicates a particular vessel type for said connector and for which said connector is adapted. Preferably, said vessel type comprises a femoral artery. Alternatively, said vessel type comprises an aorta.

In a preferred embodiment of the invention, said packaging indicates a particular vessel size for said connector and for which said connector is adapted. Alternatively or additionally, said packaging indicates a particular vessel wall thickness for said connector and for which said connector is adapted. Preferably, said ring-like shape has an axial extent smaller than said wall thickness.

In a preferred embodiment of the invention, said packaging indicates a particular connection geometry for said connector and for which said connector is adapted. Preferably, said geometry is a side-to-end geometry.

In a preferred embodiment of the invention, said packaging indicates a particular oblique angle geometry for said connector and for which said connector is adapted.

In a preferred embodiment of the invention, said at least one spike is cut out of an opposing spike of said connector.

In a preferred embodiment of the invention, at least one of said ring segments comprises a plurality of axially spaced elements. Preferably, said plurality of elements comprises at least three elements. Alternatively, said plurality of elements comprises at least four elements. Alternatively, said plurality of elements comprises at least five elements.

In a preferred embodiment of the invention, all of said plurality of elements have a same geometry. Alternatively, at least two of said plurality of elements have mirrored geometries.

In a preferred embodiment of the invention, at least one of said plurality of elements has a single curve geometry. Alternatively, at least one of said plurality of elements has a dual curve geometry. Alternatively, at least one of said plurality of elements has at least three curves defined thereby.

In a preferred embodiment of the invention, at least one of said plurality of elements has a varying width. Alternatively, all of said plurality of elements have a constant width.

In a preferred embodiment of the invention, the connector comprises a strain dissipation element at a point of connection of at least one of said elements and a spike element to which said ring segment is attached. Preferably, said strain dissipation element comprises a thickening of said axially spaced element. Preferably, said thickening defines an aperture.

There is also provided in accordance with a preferred embodiment of the invention, a method of everting a blood vessel, comprising:

engaging a tip of said vessel at a plurality of points around its circumference;
inverting said tip by inverting said points; and
pulling said inverted points towards a distal end of said blood vessel. Preferably, said plurality comprises four points. Alternatively or additionally, said engaging comprises engaging using forceps and where said inverting comprises rotating said forceps. Alternatively or additionally, said pulling comprises pulling different ones of said points different amounts.

There is also provided in accordance with a preferred embodiment of the invention, apparatus for graft eversion of a graft over a shaft having a tip, comprising:

a handle for engaging said shaft;
a plurality of forceps arranged to engage a tip of said graft where it protrudes form said shaft; and
a plurality of joints, each one associated with one of said forceps, for rotating said forceps pulling a tip of each of said forceps axially along said shaft.

There is also provided in accordance with a preferred embodiment of the invention, a method of measuring a graft size, comprising:

mounting a tip of said graft on two extensions, one extension coupled to a spring and one extension coupled to a handle;
manipulating said handle such that said extensions separate;
reading a measurement on a scale coupled to said spring; and
selecting an anastomosis connector responsive to said read measurement. Preferably, the method comprises further manipulating said handle to stretch said graft tip.

There is also provided in accordance with a preferred embodiment of the invention, a hole puncher, comprising:

a sharp tip for forming a puncture in a blood vessel;
a shaft having a varying diameter and having a depression formed therein for engaging a wall of said blood vessel, said diameter substantially matching a diameter of said tip at one end of the shaft, said diameter increasing away from said tip for a first distance and said diameter then defining a slope of diminishing diameter towards said depression; and
an outer tube mounted on said shaft and having a tip, said outer tube having an inner diameter of said tip that is in a range of diameters defined by said slope of diminishing diameters. Preferably, said tip of said outer tube has a smaller outer diameter that a more proximal portion of said outer tube.

There is also provided in accordance with a preferred embodiment of the invention, a method of forming an oblique anastomosis connector, comprising:

providing a non-oblique anastomosis connector;
mounting said connector in a restraint;
manipulating said restraints to deform said connector to a desired degree of obliqueness; and
heat-treating said connector after said manipulation, to maintain said distortion.

Preferably, the method comprises heat-treating said connector prior to said mounting, to train a deformation of a spike portion of said connector.

There is also provided in accordance with a preferred embodiment of the invention, a side mounted delivery system, comprising:

a handle including an opening in its side;
a graft delivery tool adapted to fit through said opening; and
a groove and projection mechanism slidably interconnecting said tool and said handle.

Preferably, the system comprises a snap-lock mechanism for axially fixing said handle relative to said tool.

BRIEF DESCRIPTION OF THE DRAWINGS

Particular embodiments of the invention will be described with reference to the following description of preferred embodiments, in conjunction with the figures. The figures are generally not shown to scale and any measurements are only meant to be exemplary and not necessarily limiting. In the figures, identical structures, elements or parts which appear in more than one figure are preferably labeled with a same or similar number in all the figures in which they appear, in which:

FIGS. 2A–2E illustrate a deployment method for the connector of FIG. 1, in accordance with a preferred embodiment of the invention;

DETAILED DESCRIPTION OF PREFERRED EMBODIMENTS

Figure 1:
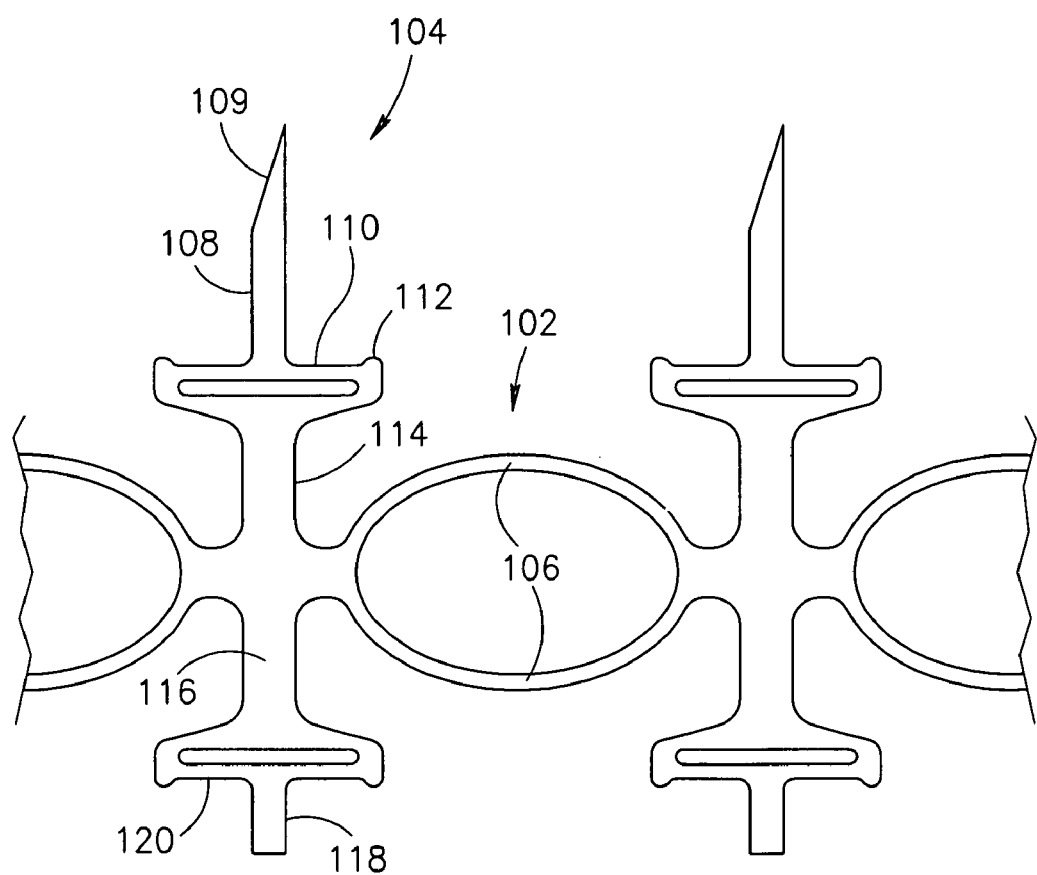
FIG. 1 is plan view of a part of a pivot-bar based anastomotic connector, in accordance with a preferred embodiment of the invention.

FIG. 1 is plan view of a part of a pivot-bar based anastomotic connector 100, in accordance with a preferred embodiment of the invention. Connector 100 is generally ring shaped, formed of a plurality of ring segments 102 and a plurality of spike elements 104 interspersed between the ring segments. It is noted however, that other connector designs, can be used, for example, the spike elements being independent of the ring segments.

A ring segment forms part of the ring structure of the connector and is typically, but not always, radially compressed, to allow easier insertion into a blood vessel. In a preferred embodiment of the invention, each ring segment 106 comprises a plurality of side-by-side elements 106, which are preferably elastic.

A spike element supports one or more opposing spikes, for example spikes 118 and 108 as shown. Spike 108 is shown with a sharp tip 109, for penetrating a graft vessel, as will be explained below with respect to FIG. 2.

A particular feature of connector 100 is that one or both of spikes 108 and 118 are mounted on a pivot bar 110 or 120, such that the spike can be extended into the figure plane without substantially bending the spike, only by twisting the pivot bar. Furthermore, the amount of distortion of the pivot bar is considerably smaller than that of a comparable in-line hinge, such as is formed by a bending of the spike. Thus, the deformation is less likely to cause hinge failure and/or a hinge can be configured to also apply greater force to the spike.

Although the spikes are shown mounted at the center of their pivot bars, this is not essential.

In connector 100, the pivot bars 110 and 120 are shown are being axially spaced from the connector by extensions 114 and 116, respectively. However, as will be shown in alternative embodiments below, this is not required.

A joint 112 attaches pivot bar 110 to extension 114. In this joint, the spacer is made thicker than the pivot bar, to prevent undesirable twisting of the spacer or any part of the connector other than pivot bar 110. Other variations of joints will be described below. It is noted, that strengthened or weakened portions may be provided at other points along the pivot bars, besides at their ends, to control where deformation takes place.

In a preferred embodiment of the invention, the pivot bar is not a load bearing structure or a radially expanding structure, so that the forces applied to the spike can be independent of the radial expansion forces. Another potential advantage of this separation is that the radial expansion of connector 100 as a whole does not have to affect the spike positions vis-à-vis extensions and/or the rest of the connector.

Another potential advantage of pivot bars, is that the profile (e.g., protrusions from the anastomosis location) of the connector can be reduced.

Another potential advantage, realized in spike 118, is that the spike does not need to penetrate the blood vessel at all. Rather, the force applied by the pivot bar is sufficient to hold the spike against the blood vessel (as shown below in FIG. 2), without penetrating it.

Figure 2A:
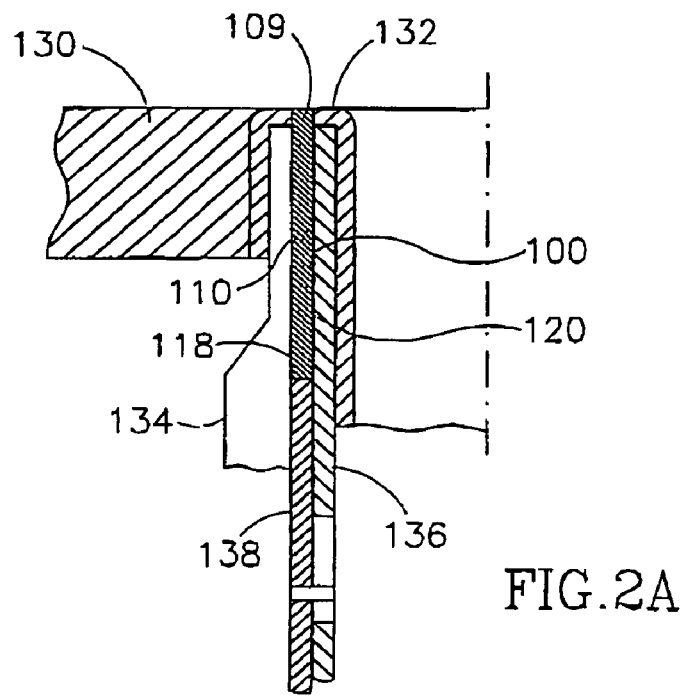

FIGS. 2A–2E illustrate an exemplary deployment method for connector 100, in accordance with a preferred embodiment of the invention. Connector 100 is preferably heat trained to have a resting configuration as shown in FIG. 2E, with spikes 108 and 118 extending perpendicular to the connector surface.

FIG. 2A shows a connector 100 with both spikes axially aligned, mounted between a holder 134 and a graft cover 136. A graft 132 is provided everted over graft cover 136 and connector 100, and inside an aperture in the wall of a "side" vessel 130. A base tube 138 maintains connector 100 in its axial position relative to the rest of the delivery system.

Figure 2B:
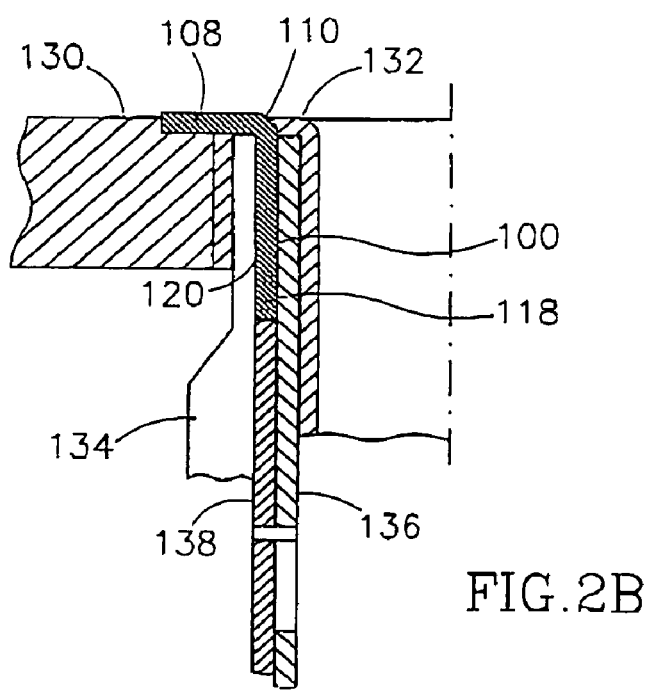

As shown in FIG. 2A, tips 109 of spikes 108 transfix graft 132, at its eversion. In FIG. 2B, the base tube 138 is advanced relative to holder 134 and cover 136, so that spike 108 advances into the aperture in vessel 130 and reverts to its resting configuration perpendicular to connector 100. Since most, if not all of the bending is in pivot bar 118, the side profile of the extended spike can be substantially perpendicular. Tips 109 may be trained to be slightly bent towards the near vessel wall, to prevent them from protruding into vessel 130.

In FIG. 2C, holder 134 is retracted, allowing connector 100 to expand radially, at its ring segments 102.

In FIG. 2D, holder 134 is retracted even more, releasing spikes 118 to bend perpendicular to connector 100. As a result, vessel 130 is grasped between spikes 108 and spikes 118. It is noted that spikes 118 do not penetrate and blood vessel, while spikes 108 only penetrate graft 132, not vessel 130. Alternatively, spikes 108 may extend directly into the side of vessel 130.

In FIG. 2E, graft cover 136 is retracted and the anastomosis is completed.

In a preferred embodiment of the invention, the spikes and spike tips are designed to support vessel 130. In one exemplary embodiment, the spikes are wide. Alternatively, the spikes are roughed on their inner surface where they contact vessel 130. Alternatively, the spike tip may be wider than the spike, for example to define a contact pad between the spike and vessel 130.

Connector 100 is preferably formed of a elastic, superelastic or shape-memory material, such as Nitinol. However, connector 100 may alternatively be plastically deformed. In one example, holder 134 engages spikes 108, when it is retracted, it bends spikes 108, by twisting pivot bar 110. Once spikes 108 are bent sufficiently, holder 134 may disengage the spikes. A suitable holder tip for engaging and disengaging is shown, for a different purpose, in FIG. 9B. When the tip is rotated, the engaged spike is released.

Figure 3:
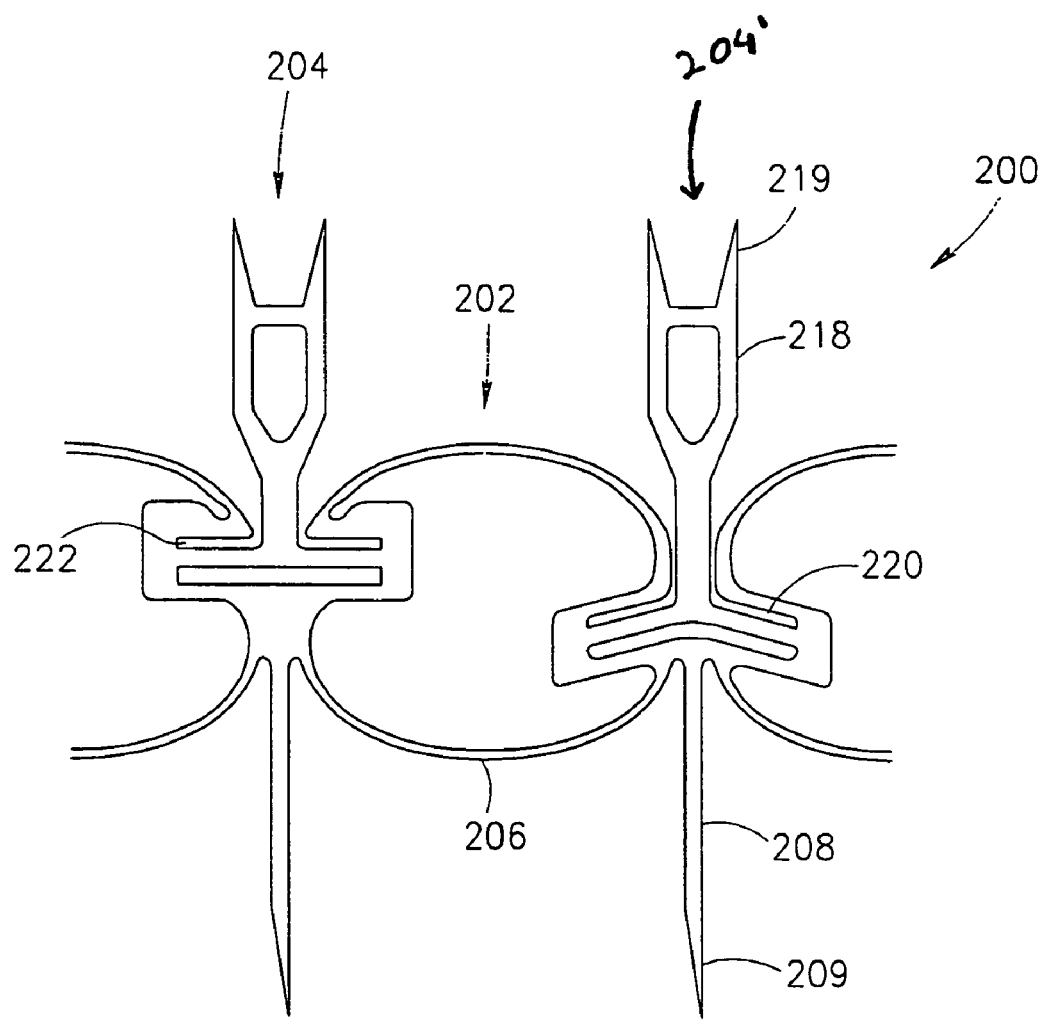
FIG. 3 is plan view of a part of another pivot-bar based anastomotic connector, in accordance with an alternative preferred embodiment of the invention.

FIG. 3 is plan view of a part of a pivot-bar based anastomotic connector 200, in accordance with an alternative preferred embodiment of the invention.

Similar to connector 100, connector 200 comprises a plurality of ring segments 202, comprising two arcs 206 and a plurality of spike elements 204, each comprising a spike 208 and a spike 218. It is noted that a particular spike element 208 does not need to include two opposing spikes and may include one or more than one spike in each axial direction.

This connector, as are other embodiments described herein, is selected to exemplify a plurality of design features. A connector in accordance with a preferred embodiment of the invention is not to be construed as being limited to the particular mix of features illustrated. Rather, the embodiments were chosen to illustrate several features in each embodiment, with the understanding that other embodiments within the scope of the invention can contain any selection of features from any of the embodiments shown.

One feature of connector 200 is that a pivot bar 220 of spike 218 is within the axial extent of ring segment 202. Thus connector 200, when deployed, can have a smaller axial extent than connector 100. In the embodiment shown, spike 208, which may be a forward spike, does not have a pivot bar and the spike itself is bent for deployment.

Another feature exemplified by connector 200, is that the pivot bars for two adjacent spike segments 204 and 204' are not at the same axial position. Thus, the pivot bars of adjacent spike elements do not contact during radial compression of connector 200.

Another feature of connector 200, is that a pivot bar 220 of spike 218 is not straight. As shown, the pivot bar is V shaped, however, a sine shape or a zigzag shape could also be provided. Spike 218 is preferably, but not necessarily, attached at the bend in pivot bar 220. A potential advantage of the V shaped designed showed is that a greater force can be applied over part of the bending positions of spike 218, than can be with a similar straight pivot bar. Alternatively, the pivot bar may be tilted to provide space for axial compression, but remain straight.

Another feature of connector 200 is that the mechanism supporting the pivot bars forms substantially square corners that jut into the neighboring ring segments. Alternatively, these corners may be rounded. Optionally, the pivot bar is bent to conform with the connector surface, however, this is not essential, especially in those connectors where the pivot bar is coupled to the connector at only a single point.

Another feature of connector 200, which will be illustrated in FIG. 4 that describes the deployment, is that the spikes are both bent and twist around the pivot bars. Thus, spikes 218 include a forked tip 219, for spearing vessel 130. However, this spearing can be at an angle significantly shallower than 90°, for example 60° or 30°.

Figure 4A:
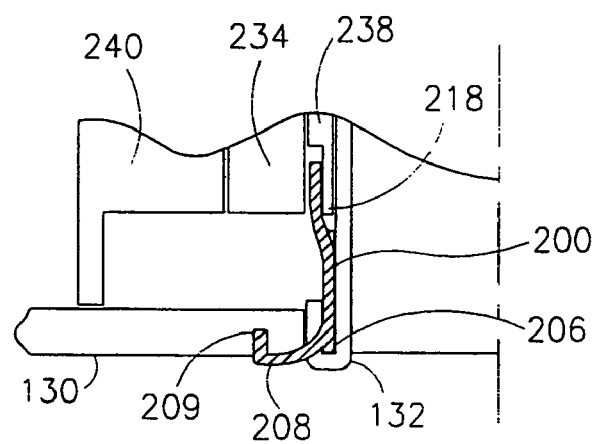
FIGS. 4A–4C illustrate a deployment method for the connector of FIG. 3, in accordance with a preferred embodiment of the invention.
Figure 4B:
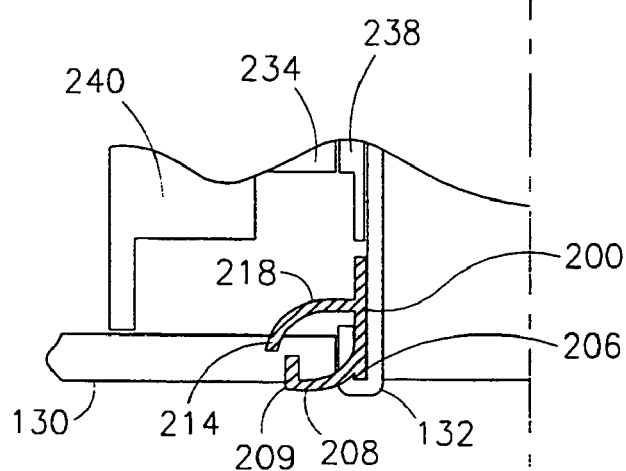
Figure 4C:
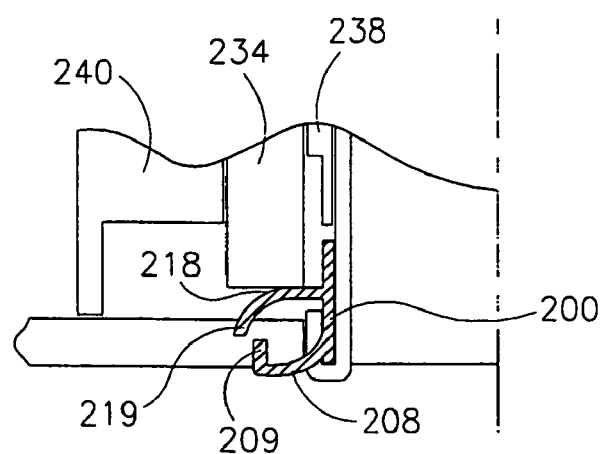

FIGS. 4A–4C illustrate a deployment method for connector 200, in accordance with a preferred embodiment of the invention.

FIG. 4A shows connector 200 after its forward spike 208 is released to engage vessel 130. A method similar to that shown in FIG. 2 may be used for releasing the spikes (which may be super-elastic), or other methods, for example as described in the above referenced PCT applications, can be used.

Spikes 218 are preferably held between a connector holder 238 and a outer tube 234, during and shortly following the engagement of vessel 130 by spikes 208. A connection positioner 240 may be provided to control the position of connector 200 relative to vessel 130 and provide a counter-force for retracting connector 200 so that spikes 209 engage vessel 130.

In FIG. 4B, outer tube 234 is retracted, freeing spike 218 to bend. As shown, both spike 218 and pivot bar 220 bend, with the result that spike tip 219 engages vessel 130.

In FIG. 4C, an optional step of advancing outer tube 234 is illustrated, this advancing further bends spike 218 and strengthens the engagement of vessel 130.

Figure 4D:
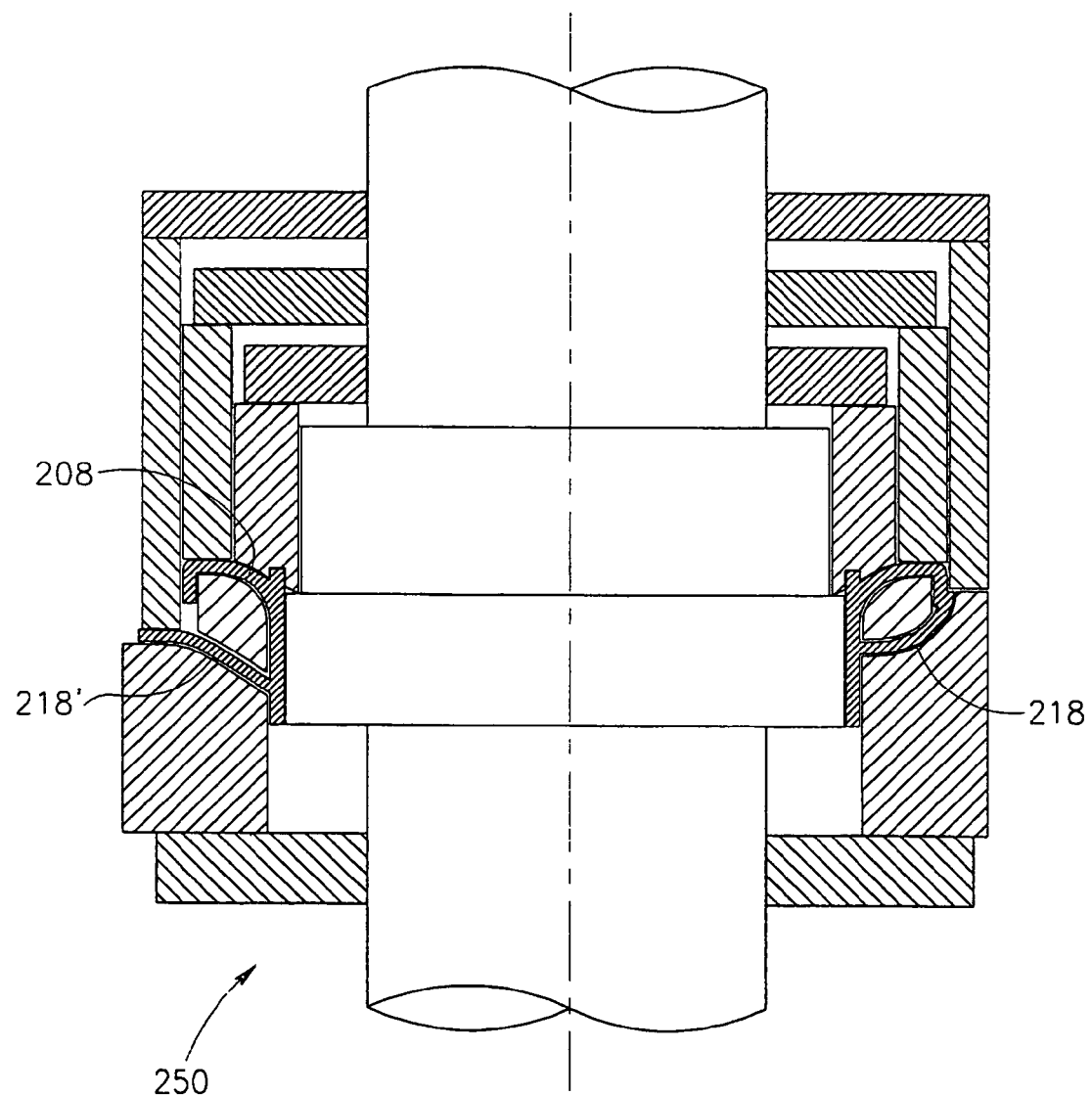
FIG. 4D is a cut-sectional view of an heat-treating device suitable for pivot-bar based anastomosis connectors, in accordance with a preferred embodiment of the invention.

FIG. 4D is a cut-sectional view of an heat-treating device 250 suitable for pivot-bar based anastomosis connectors, in accordance with a preferred embodiment of the invention. connector 200 (or 100) is placed in device 250. This placement requires distorting the connector as shown. Device 250 is then heated to heat-treat the connector and make the new configuration its resting configuration to which the connector tends to return after distortion.

Two types of spikes 218 are shown in FIG. 4D, namely, a penetrating spike 218 is as shown in FIG. 3, and a contact spike 218' does not penetrate vessel 130. Optionally, the contact spikes are distanced from the connector center, to allow more force to be applied to vessel 130 during deployment.

A single connect may include both penetrating and contact spikes 218, as shown, or the connect may comprise only contact spikes 218' or only penetrating spikes 218.

Figure 5:
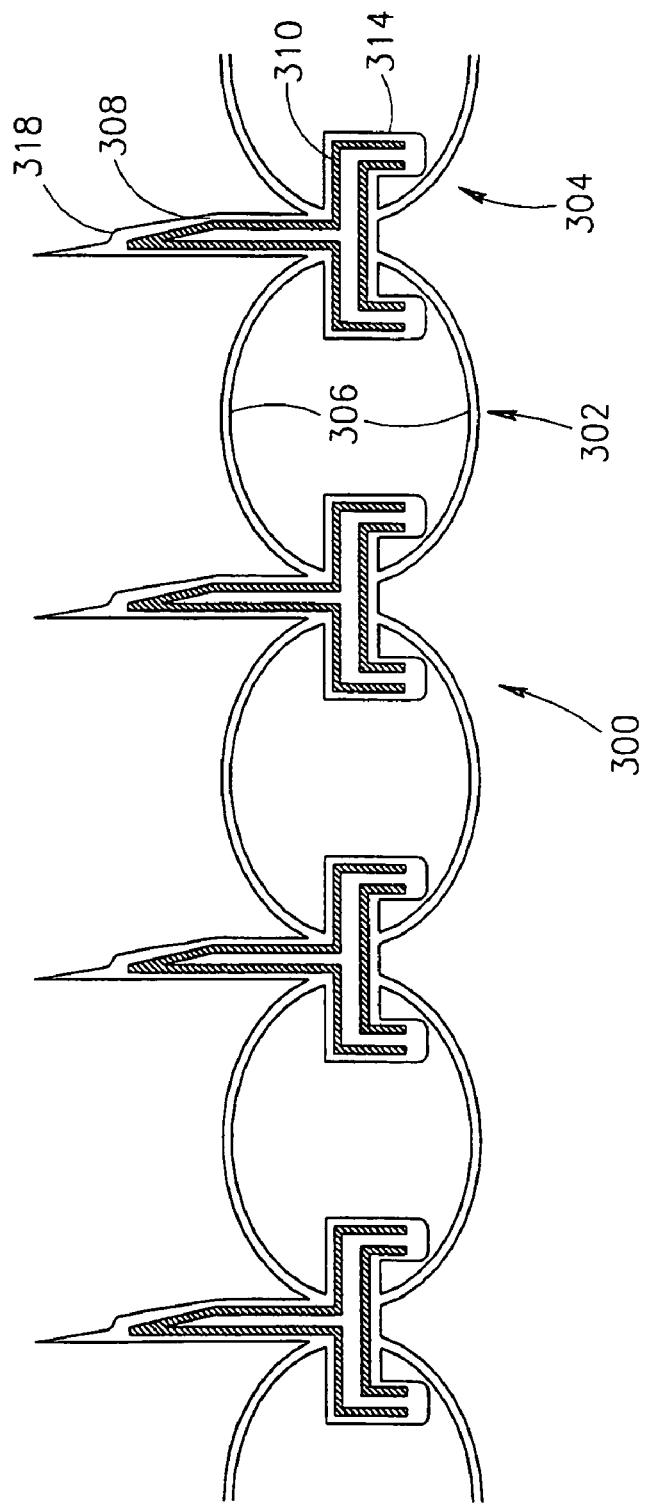
FIG. 5 is plan view of a part of a pivot-bar based anastomosis connector, featuring spikes cut out of spikes in accordance with a preferred embodiment of the invention.

FIG. 5 is plan view of a part of a pivot-bar based anastomotic connector 300, featuring spikes cut out of larger spikes in accordance with a preferred embodiment of the invention. As with the above connectors, connector 300 comprises a plurality of ring segments 302 each formed of a pair of arcs 306. A spike 308 is cut out of the body of a spike 318. A pivot bar 310 of spike 308 is mounted on optional extension tabs 314.

One feature of connector 300 is that the spikes bases are defined within the axial extent of ring segments 302.

Another featured of connector 300 is that spikes 318 are hollow, so that a smaller amount of foreign material is present and better tissue adhesion, across the spike, can be provided.

Another feature of connector 300 is that pivot bar 310 is mounted on extension tabs 314. Thus, the axial location of pivot bar 310 can be set after the connector manufacture, by bending tabs 314 a desired amount and then heat treating the device to finalize the tab location.

In the above embodiments, graft 132 is typically transfixed by spikes 108, 208 or 308. Alternatively, no such transfixing is provided. In this alternative embodiment, ring segments 306 are provided inside of the everted part of graft 132. Tabs 314 are folded back past the edge of the eversion and then optionally again forward, so that spikes 308 and pivot bar 310 are on the outside of the everted section of graft 132. Optionally, spikes 308 are defined in the center of ring segments 306, rather than between the segments, and the everted portion of graft 132 is held between ring segments 306 and pivot bar 310.

Figure 6A:
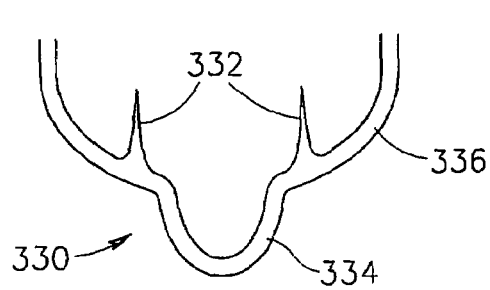
FIGS. 6A–6C illustrate various spike designs utilizing a pivot-bar or a similar hinge, in accordance with preferred embodiments of the invention.
Figure 6B:
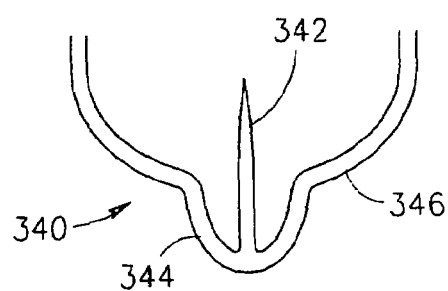
Figure 6C:
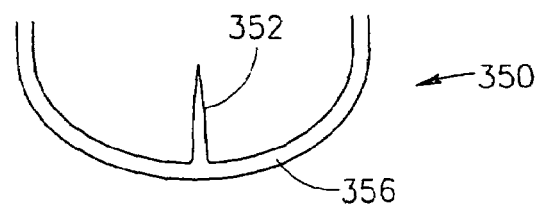

FIGS. 6A–6C illustrate various spike designs utilizing a pivot-bar or a similar hinge, in accordance with preferred embodiments of the invention. As will be shown in the embodiment of FIG. 6D, these spikes may be extended differently from the spikes described above. In particular, these spikes may be pointed towards the ring of the connector, at least during manufacture.

In FIG. 6A, a spike mechanism 330 includes a pair of spikes 332 mounted on a base 336, which base includes an extension 334. Base 336 can serve as a pivot bar, inasmuch as the rotation of spikes 332 is supported by distortion of a significant length of base 336. Extension 334 may server for holding spike 332 during insertion.

In FIG. 6B, spike mechanism 340 features a spike 342, mounted on an extension portion 344 of a base 346, possibly allowing better control of the bending and a reduction in the volume taken up the rotation of the spike.

In FIG. 6C, a spike mechanism 350 features a spike 352 mounted directly on a base 356. It is noted that various spike lengths may be provided, within the scope of the invention, the spike lengths preferably being selected to penetrate vessel 130 only a desired amount.

Figure 6D:
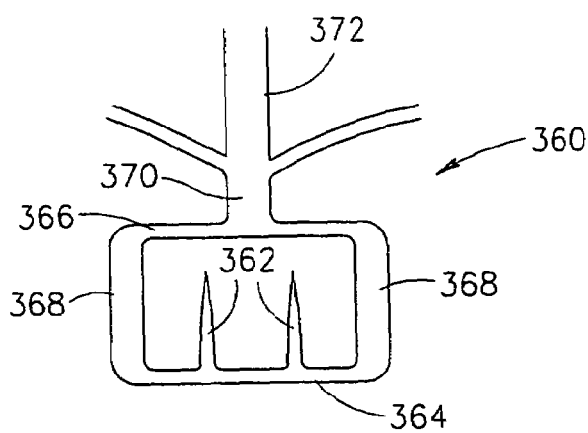
FIGS. 6D–6E illustrate a spike design utilizing two pivot bars, in accordance with a preferred embodiment of the invention.
Figure 6E:
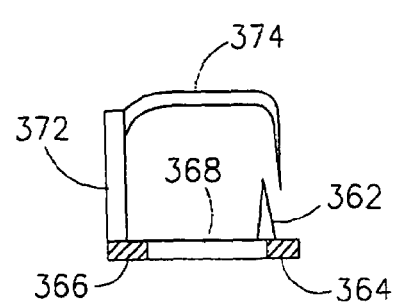

FIGS. 6D–6E illustrate a spike mechanism 360 utilizing two pivot bars, in accordance with a preferred embodiment of the invention. FIG. 6D is a plan view. Mechanism 360 has two spikes 362 mounted on a pivot bar 364. Pivot bar 364 is itself mounted, via two extensions 368 on a second pivot bar 366. A portion 370 connects mechanism 360 with the rest of a connector 372.

FIG. 6E is a side view of a deployed connector 372. Mechanism 360 is bent twice, once at pivot bar 366 and once at pivot bar 364. This allows a substantially square profile to be produced, which conforms to the blood vessels taking part in the anastomosis. Also shown is an opposing spike 374, which may be of any type.

It should be noted that a single pivot bar can be used to provide a wide range of rotation angles, such as between 15° and 180°, or even over 180°. In some embodiments, a double pivot bar is provided for large angles of rotations, however, this is not required.

Figure 7A:
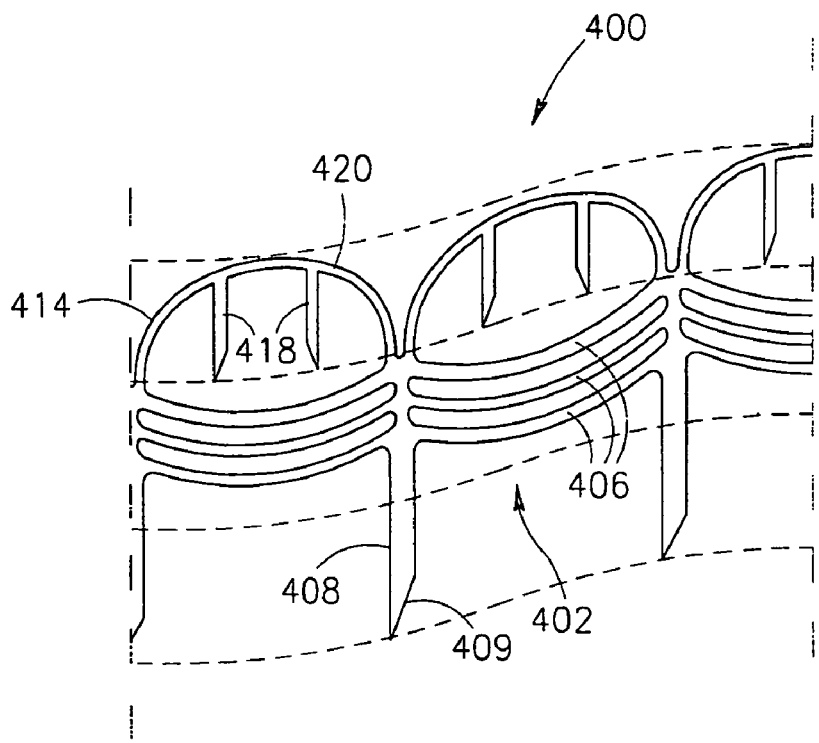
FIGS. 7A–7B illustrate an oblique anastomosis connector utilizing a pivot bar design, in accordance with a preferred embodiment of the invention.
Figure 7B:
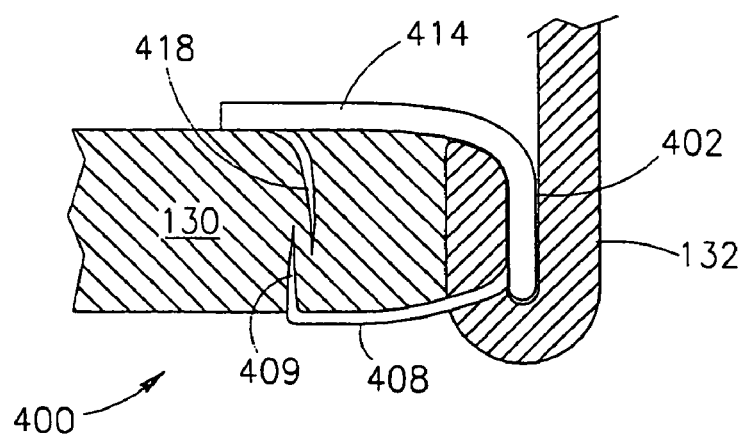

FIGS. 7A–7B illustrate an oblique anastomosis connector 400 utilizing a pivot bar design, in accordance with a preferred embodiment of the invention. FIG. 7A is a plan view of a part of connector 400. Connector 400 comprises a plurality of ring segments 402, each comprises a plurality of arc sections 406. A forward bending spike 408 is provided, with a tip 409. A pair of backward spikes 418 are mounted on a pivot bar 420. Bar 420 is separated from connector 400 by a pair of extensions 414, however, a single extension or three or more extensions could be used.

Device 400 is built to be oblique, thus, the ring segments do not lie on a straight line, but on a wavy line, preferably corresponding to the final shape of the connection. In the embodiment shown, the spikes are parallel to the connector axis. Alternatively, the spikes and/or the pivot bars may be tilted or even parallel with the axis defined by the lumen of connector 400 (this axis is perpendicular to the ring plane of the connector).

FIG. 7B is a side cross-sectional view of a deployed connector 400.

It should be noted that spikes 418 and spikes 408 can be designed to push in opposite radial directions, for example spikes 408 pushing in and spikes 418 pushing away from the anastomosis connection. Thus, the wall of vessel 130 can be radially engaged by the spikes. Alternatively, the spikes apply a stretching force to the wall of vessel 130. In either case, the spike position and force application direction can be used to isolate the rest of vessel 130 from the forces applied by the anastomosis connection, optionally, while compressing a part of the wall of vessel 130 between at least some of the spikes (not necessarily all from the same axial set) and the ring-part of the spike.

FIGS. 8A–8E illustrate various anastomosis connector designs, in accordance with preferred embodiments of the invention.

Figure 8A:
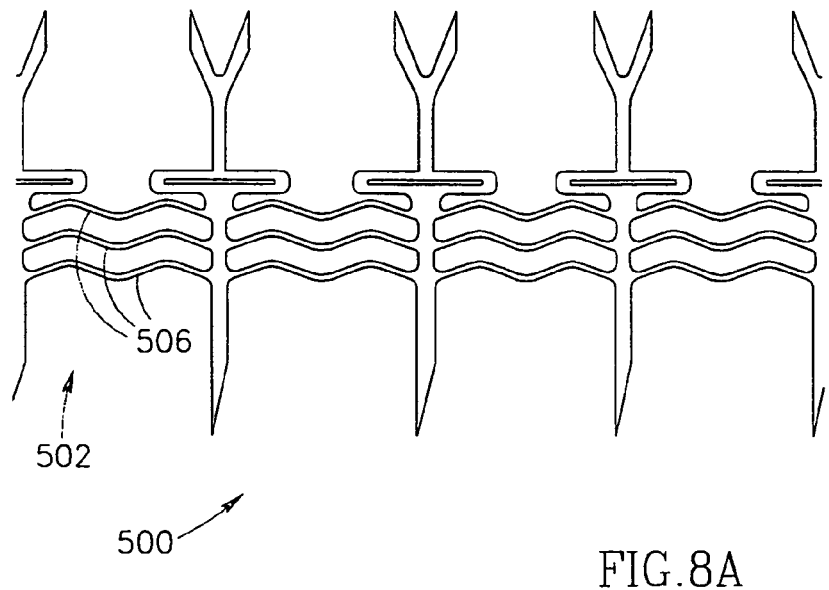
FIGS. 8A–8E illustrate various anastomosis connector designs, in accordance with preferred embodiments of the invention.

FIG. 8A is a plan view of a portion of an anastomosis connector 500, in which each ring segment 502 is formed of a plurality of zigzag elements 506. Elements 506 may have a constant width or their width may vary. One expected benefit of using zigzag elements is that the connector is less likely than an arc-based device to distort in an unexpected manner. Another potential benefit of zigzag ring segments is that the force applied by the expanding ring can be better matched to the needs of the anastomosis.

Figure 8B:
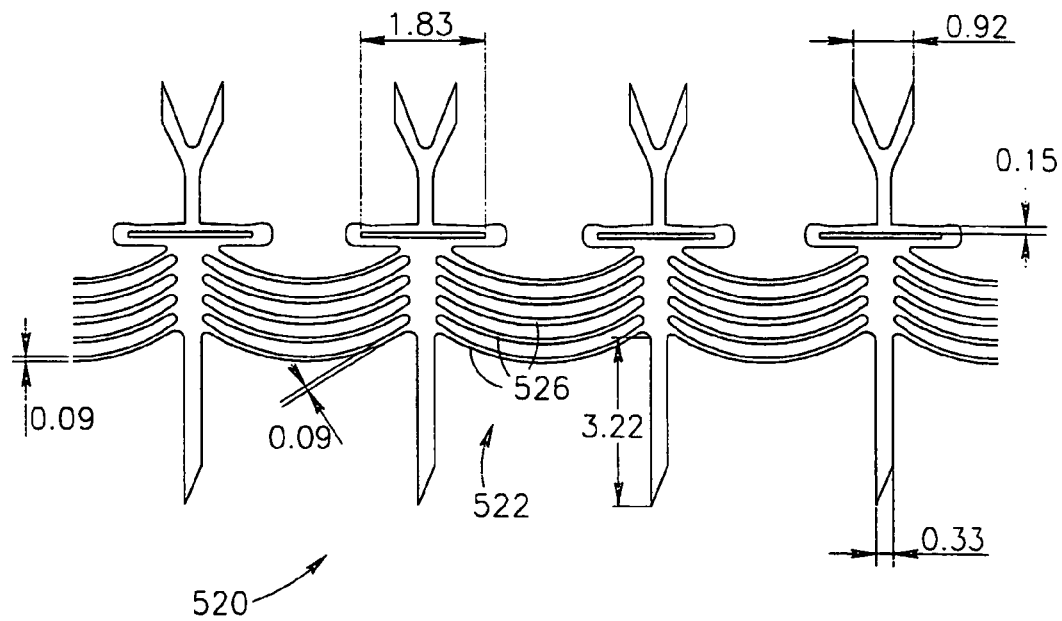

FIG. 8B is a plan view of a portion of an anastomosis connector 520, in which each ring segment 522 is formed of a plurality of arc elements 526. In connector 520, five arc elements 526 are provided. In other embodiments, a different number of arc-elements may be used, for example three or four.

The term arc-element is used for convenience, the actual curve of each element 506 need not be that of an arc of a circle, for example being a spline or a segment of an ellipse. Alternatively or additionally, the different elements may have different shapes and/or widths, for example the radius of curvature increasing in an axial direction.

In a typical manufacturing process, two connectors overlap in the raw material, for example the spikes of one connector interleaved with the spikes of a next connector. Thus, the manufacturing process can be more efficient with respect to waste material.

Figure 8C:
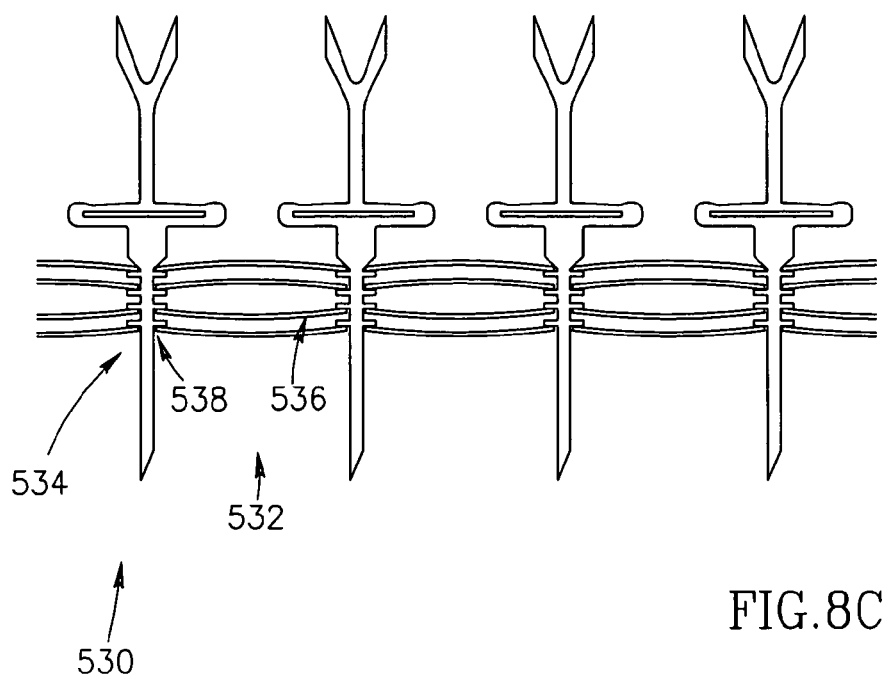

FIG. 8C is a plan view of a portion of an anastomosis connector 530, in which each ring segment 532 is formed of a plurality of arc elements 536. In connector 530, four arc elements are provided, arranged in the form of two concentric near ellipses. At the point of contact between an arc-element 536 and a spike element 534, a strengthening or a loop 538 is preferably provided, to prevent stress related damage from occurring at that point.

Figure 8D:
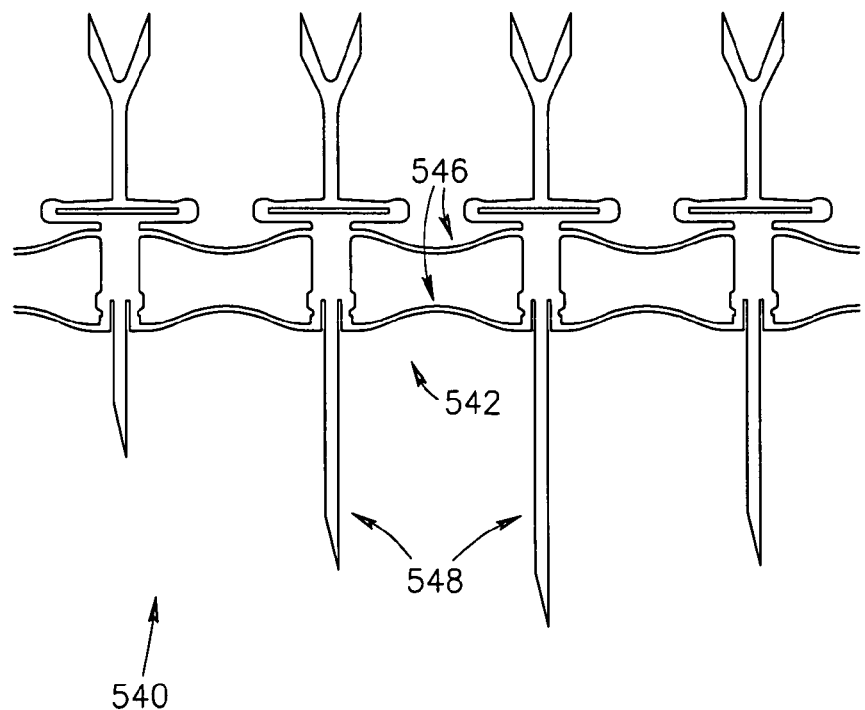

FIG. 8D is a plan view of a portion of an anastomosis connector 540, in which each ring segment 542 is formed of a plurality of recurved elements 546. In connector 540, two such recurved elements are provided. As shown, a plurality of forward spikes 548 have different lengths. These different lengths may be used for forming an oblique anastomosis connector and/or for oblique anastomosis connections, as described below, for example. The number of curves in the recurved element can be greater, for example, being three, four or more.

Figure 8E:
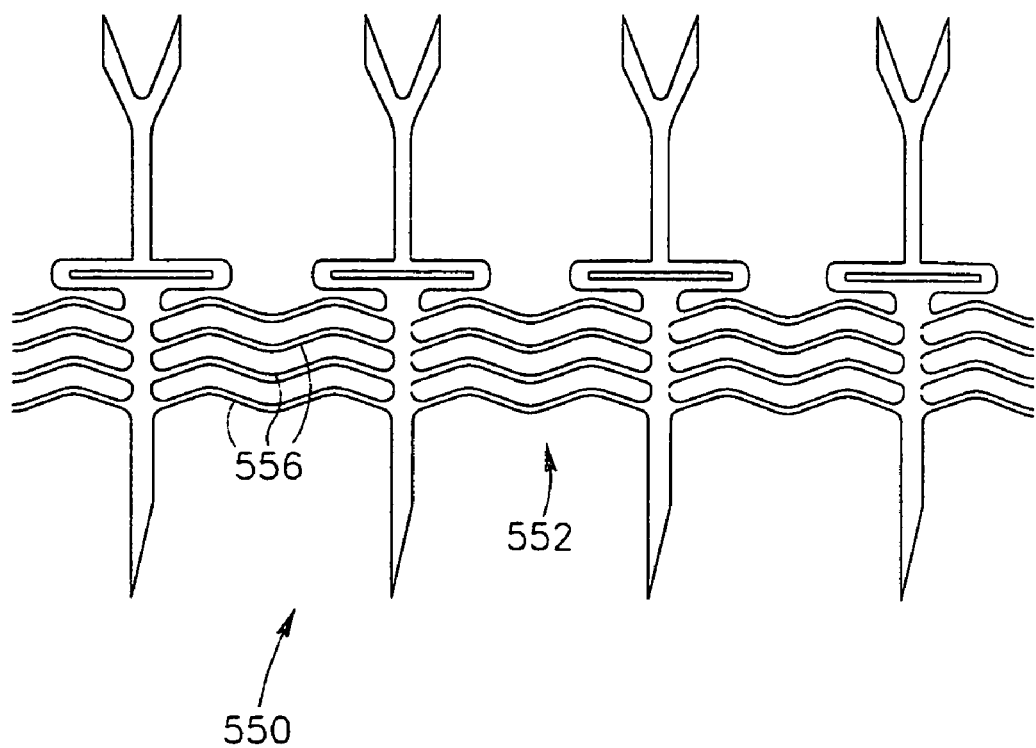

FIG. 8E shows a connector 550 similar to connector 500 of FIG. 8A, in which four, rather than three zigzag elements 556 are provided.

It should be appreciated that the number, shape, thickness and mechanical working of the ring segments are determined based on a desired mechanical behavior. Typically, but not necessarily, the desired parameters are:
  (a) withstanding stress fracture;
  (b) sufficient radial force against vessel 130;
  (c) provision of a seal against leakage;
  (d) matching of vessel 130 wall thickness; and/or
  (e) pulsile and other characteristics of the vessel for which they are designated.

In addition, to the above variations, the ring segment design may vary between elements in a single connector, for example being alternately arc elements and zigzag elements.

In a preferred embodiment of the invention, structural elements are added to the connector to prevent to large an increase in radius, for example by providing struts or wires that interconnect neighboring spike elements and prevent them from separating too much.

Oblique connectors may be formed by obliquely cutting metal tubes or sheet metal. Alternatively, an oblique connector is formed by manufacturing a perpendicular connector and then distorting it to make it oblique. In an exemplary embodiment, the above connectors may be formed by cutting a suitable Nitinol tube, for example having an outer diameter of 5.3 mm and having a material thickness of 0.18 mm.

Figure 9A:
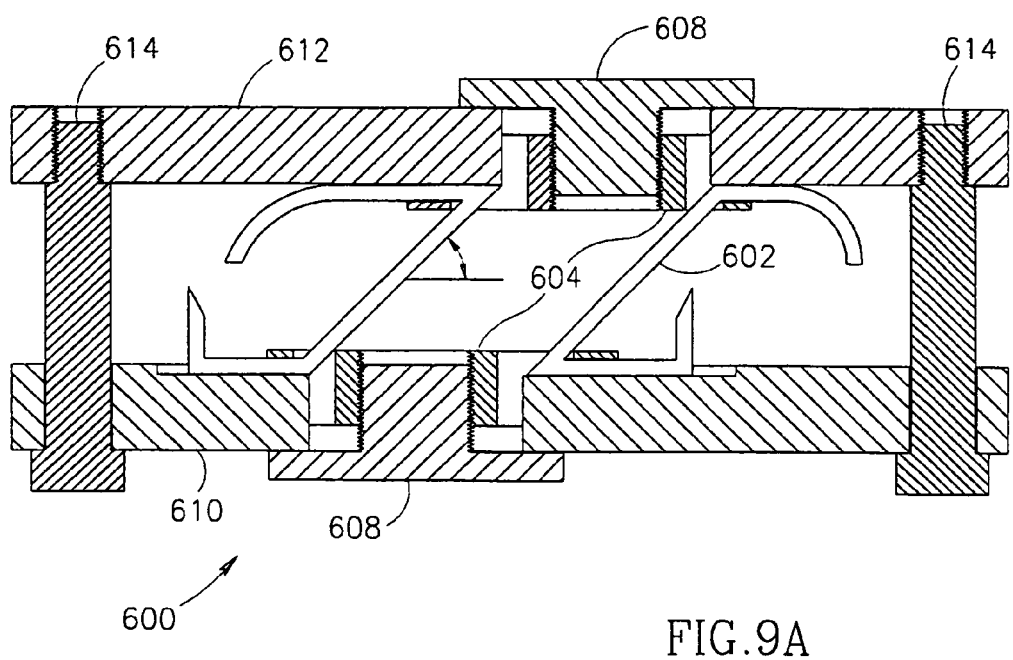
FIGS. 9A and 9B illustrate a connector-bending device, in accordance with a preferred embodiment of the invention.
Figure 9B:
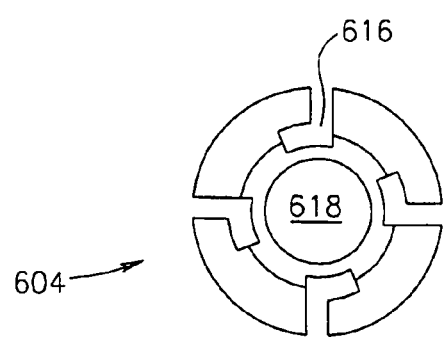

FIGS. 9A and 9B illustrate a connector-bending device 600, in accordance with a preferred embodiment of the invention. FIG. 9A is a side cross-sectional view of device 600. A connector 602, preferably after it is heat-treated to learn a new resting configuration of its spikes, is mounted on two tools 604, each of which engages the spikes of one side of connector 602. A screw 608 is used to fix one tool 604 to a bottom base 610 and another screw 608 is used to fix the other tool 604 to a top base 612. The two bases are moved relative to each other, such that connector 602 is distorted. The two bases are then attached to each other using screws 614 and the entire device is placed in an oven for additional heat-treating.

FIG. 9B is a top view of tool 604, showing L shaped slots for engaging the spikes of connector 602 and an inner-threaded aperture for engaging screw 608.

Figure 10:
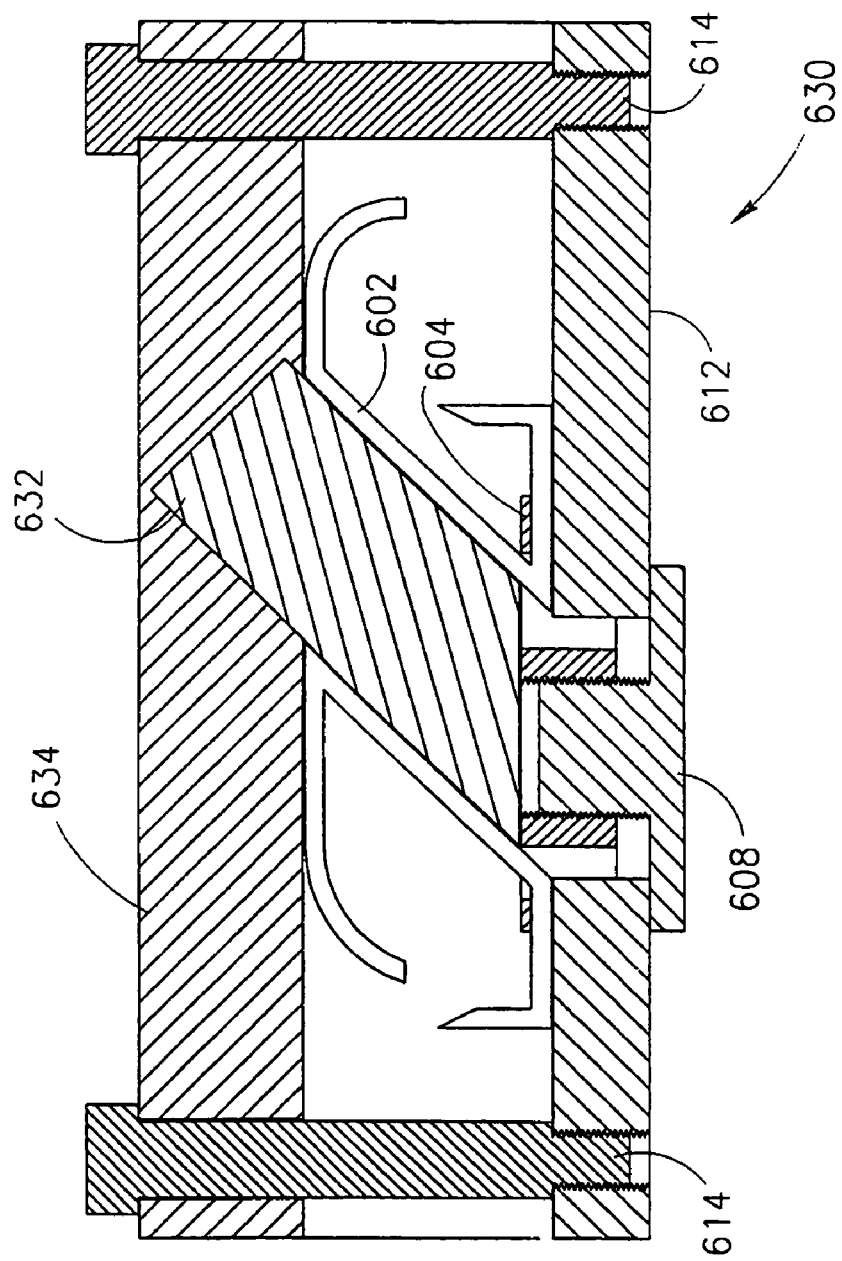
FIG. 10 illustrates an alternative connector-bending device, in accordance with a preferred embodiment of the invention.

FIG. 10 illustrates an alternative connector bending device 630, in which a same base 612, screw 608 and tool 604 are used to engage one end of connector 602. However, the connector is distorted by inserting a stylet 632 into the lumen of connector 602. The cross-section of stylet 632 can be any desired cross-section. A second based 634 fixes the stylet in place and, the device and connector are placed in an oven for heat-treating.

Figure 11:
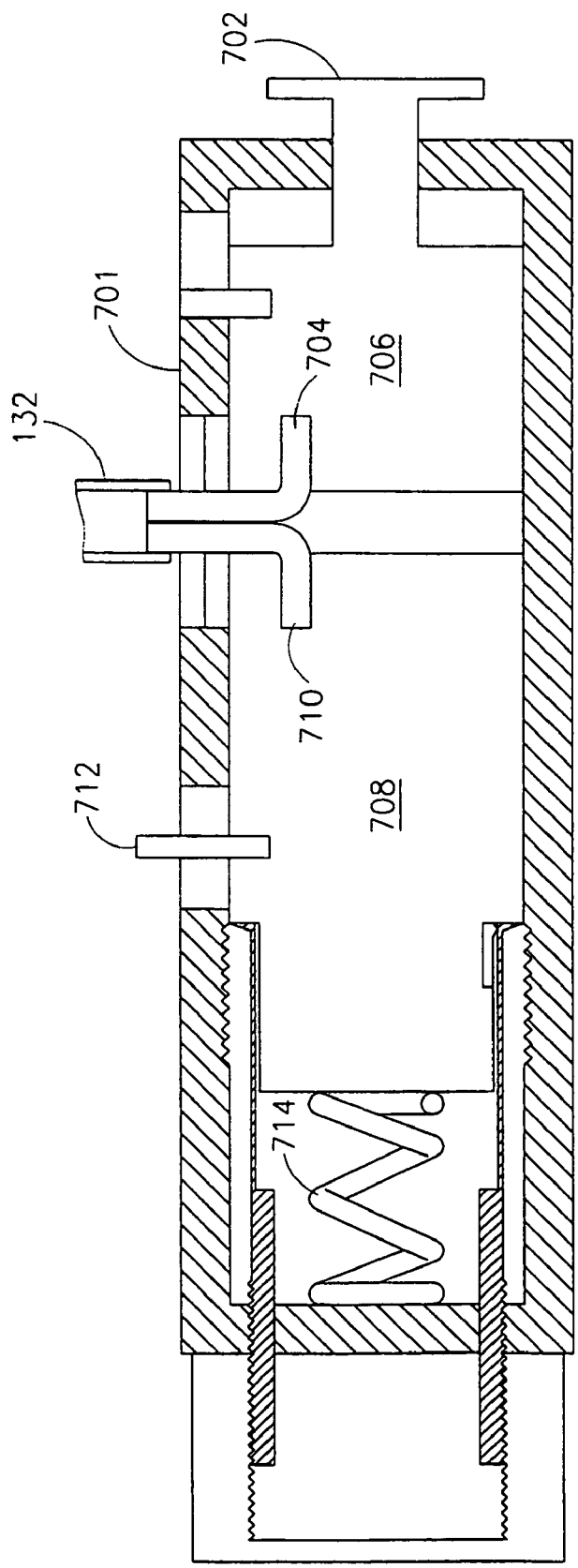
FIG. 11 is a cross-sectional view of a graft measurement and/or stretching device in accordance with a preferred embodiment of the invention.

FIG. 11 is a cross-sectional view of a graft measurement device 700, in accordance with a preferred embodiment of the invention. Device 700 comprises a body 701 having a handle 702 at one end thereof. A graft 132 is placed on two projections 704 and 710. Projection 704 is coupled to a piston 706 that is fixed to handle 702. Projection 710 is coupled to a piston 708, which is coupled to body 701 via a weak spring 714. A scale 712 is mounted on piston 708.

In operation, an extension force applied to handle 702 is coupled to piston 708 via graft 132. The diameter of graft 132 affects the measurement shown on scale 712. An additional extension of handle 702, possibly until a block, stretches graft 132 in preparation for eversion. It will be appreciated by a person skilled in the art that other ways of coupling the diameter of the graft to the extension of a weak spring can also be used to the same effect. It is noted that over-stretching of graft 132 can be prevented by selecting a spring that yields before the graft does or by selecting a spring that even when stretched to its maximum allowed length does not apply a force above a safety threshold.

Figure 12A:
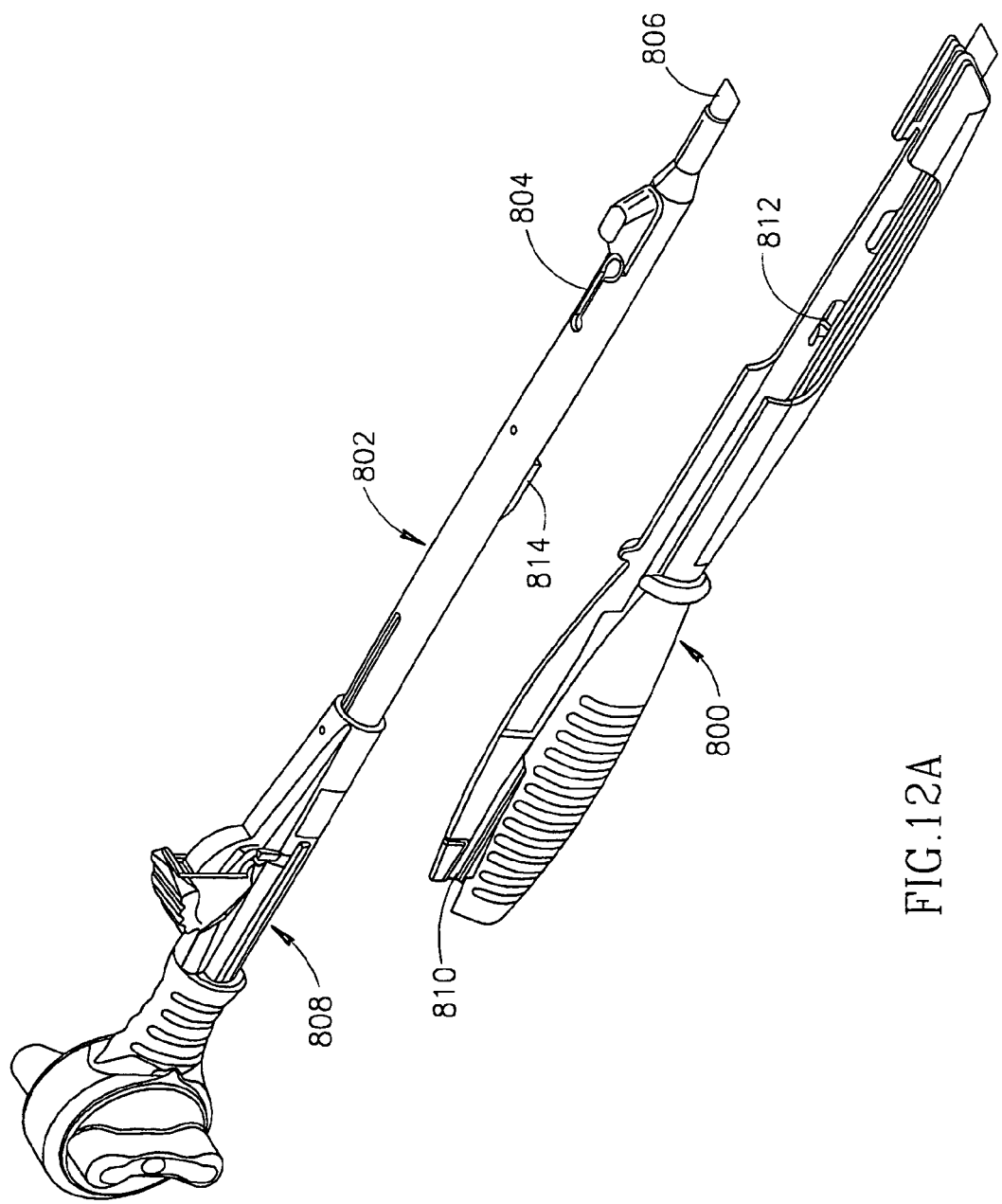
FIGS. 12A–12C illustrates a side-mounted anastomosis delivery system, in accordance with a preferred embodiment of the invention.
Figure 12B:
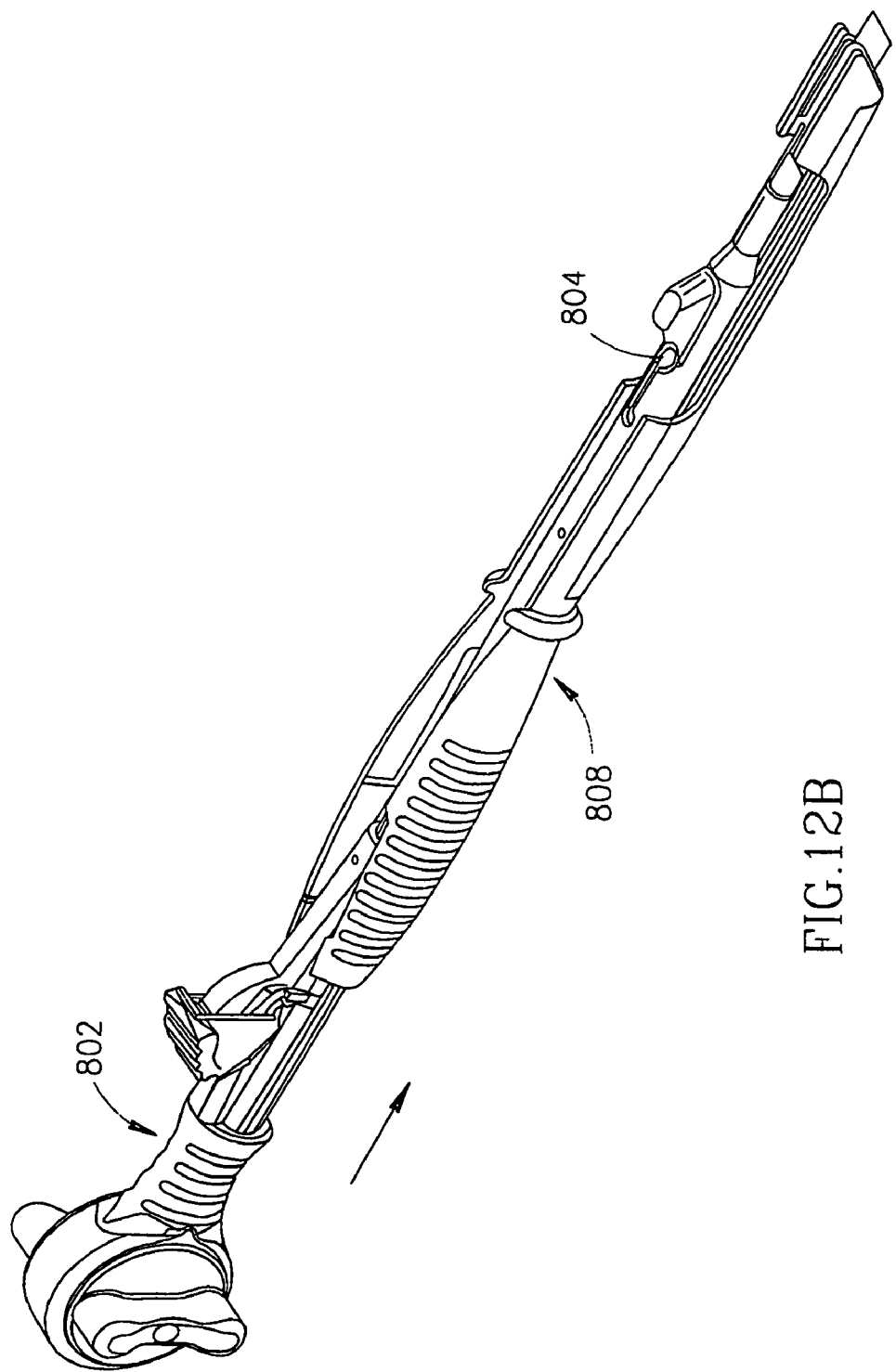
Figure 12C:
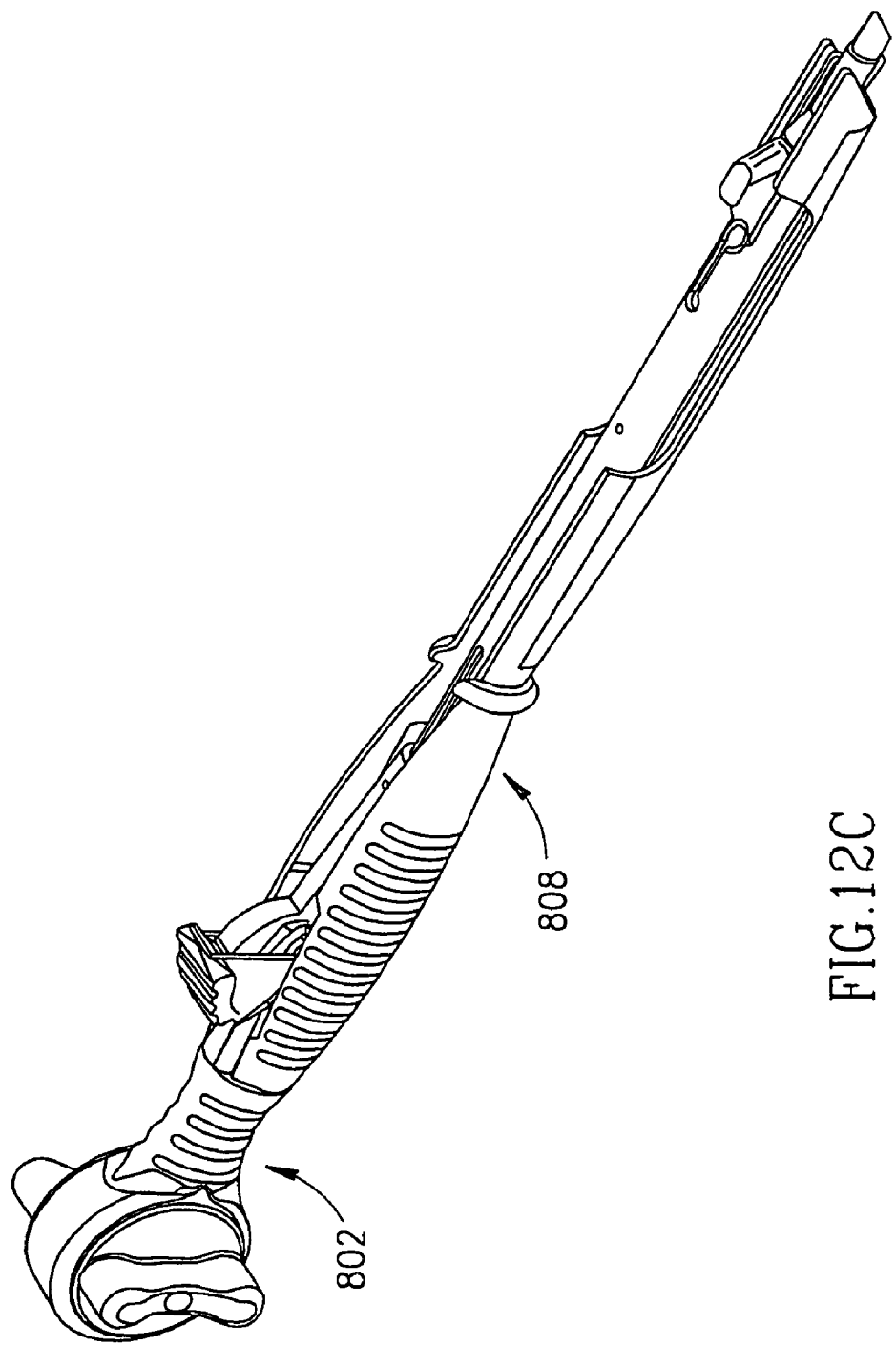

FIGS. 12A–12C illustrates a side-mounted anastomosis delivery system, in accordance with a preferred embodiment of the invention. In a preferred embodiment of the invention, a single handle 800 is used to provide various tools to the anastomosis location. Two exemplary tools are a graft delivery tool 802 and a hole puncher (not shown).

In a preferred embodiment of the invention, the tools are loaded into handle 800 from the side of handle 800. A slide and snap mechanism is shown as an exemplary method of achieving side loading. Tool 802 has at least one rail 808 defined on it and handle 800 has a matching groove 810. A projection 814 on tool 802 matches a projection 812 in handle 800. The grooves and the projection may be switched between the handle and the tool.

FIG. 12A shows handle 800 separated from tool 802. In FIG. 12B, groove 810 engages rail 808. In FIG. 12C, tool 802 is advanced enough so that projections 814 and 812 interlock.

Tool 802 may be removed by applying sufficient retraction force, to overcome the resistance of the projections, either bending them away or breaking them (for a one-time device).

In operation, a graft 132, such as a vein, is inserted into an opening 804 in tool 802 and exits at its open tip 806. Tip 806 with the graft on it is then inserted into an aperture in vessel 130 (e.g., FIG. 2). One potential advantage of side loading the graft holding tool 802 into handle 800, is that the vein is less likely to be damaged by passage through handle 800, if such passage is minimized.

Another potential advantage is that it is easier to mount and navigate a short vein on a side-mounted tool. It is noted that graft mounting may be required to be performed even if the vein is still connected to the body, in which case, possibly, the vein cannot be removed from the body at all, or any significant distance.

Tool 802 can correspond, for example to the device used in FIG. 2, with tip 806 corresponding to graft holder 136.

FIGS. 13A–13F illustrate a graft eversion tool 900, in accordance with a preferred embodiment of the invention.

Tool 900 comprises a hollow shaft 902 for engaging a graft delivery tool, such as tool 802 (FIG. 8) and a plurality or forceps mounting points 904 (four shown in this exemplary embodiment, but other embodiments may have as few as one, two or three or more, such as five or six). Preferably, a forceps 906 is mounted on each mounting point 904, using a forceps mechanism 908. However, for clarity, the figures show only a single forceps in one forceps mounting mechanism. Also, graft 132 is not shown.

Figure 13A:
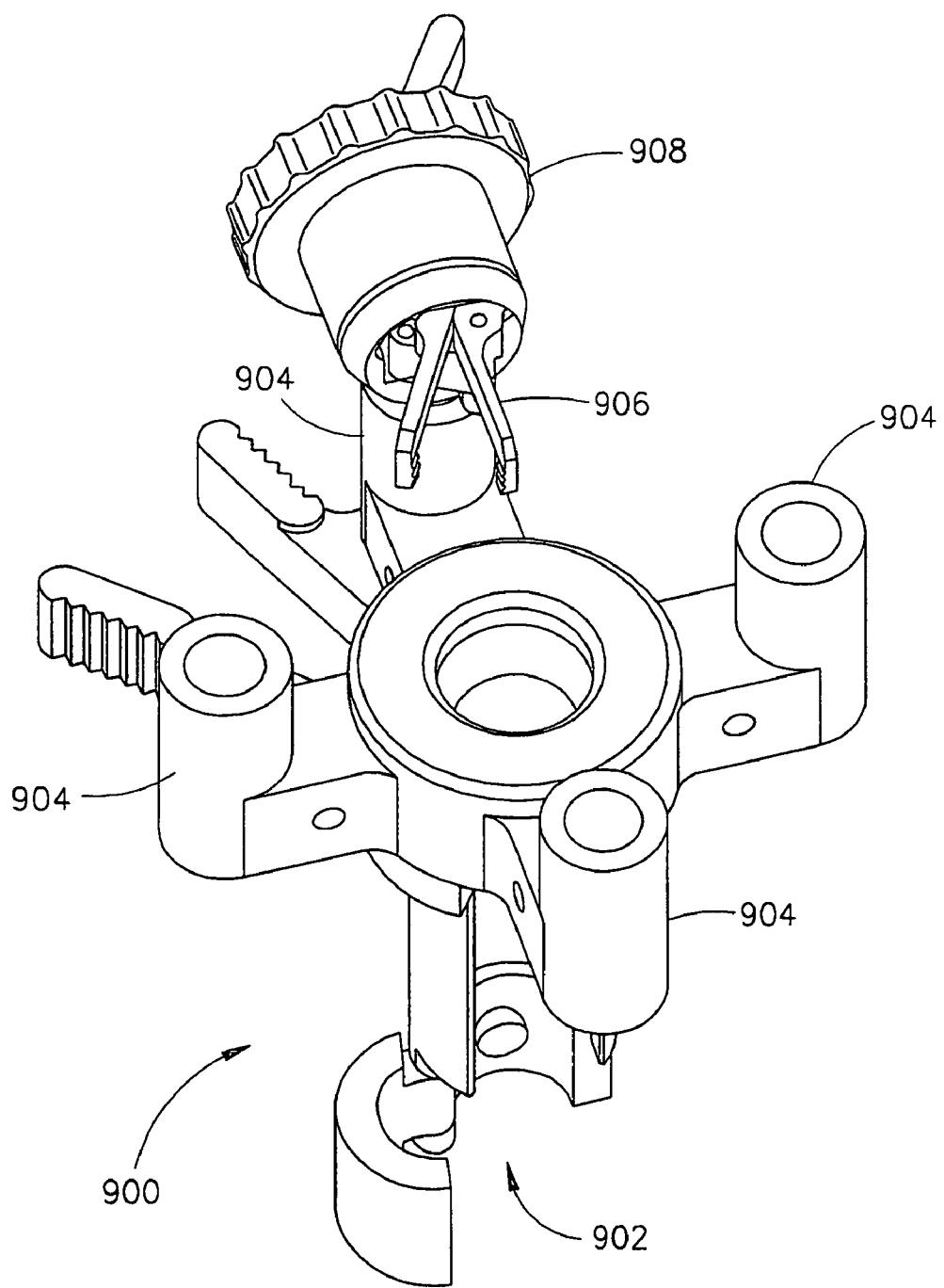
FIGS. 13A–13F illustrate a graft eversion tool, in accordance with a preferred embodiment of the invention.

FIG. 13A shows device 900 prior to the provision of tool 802.

Figure 13B:
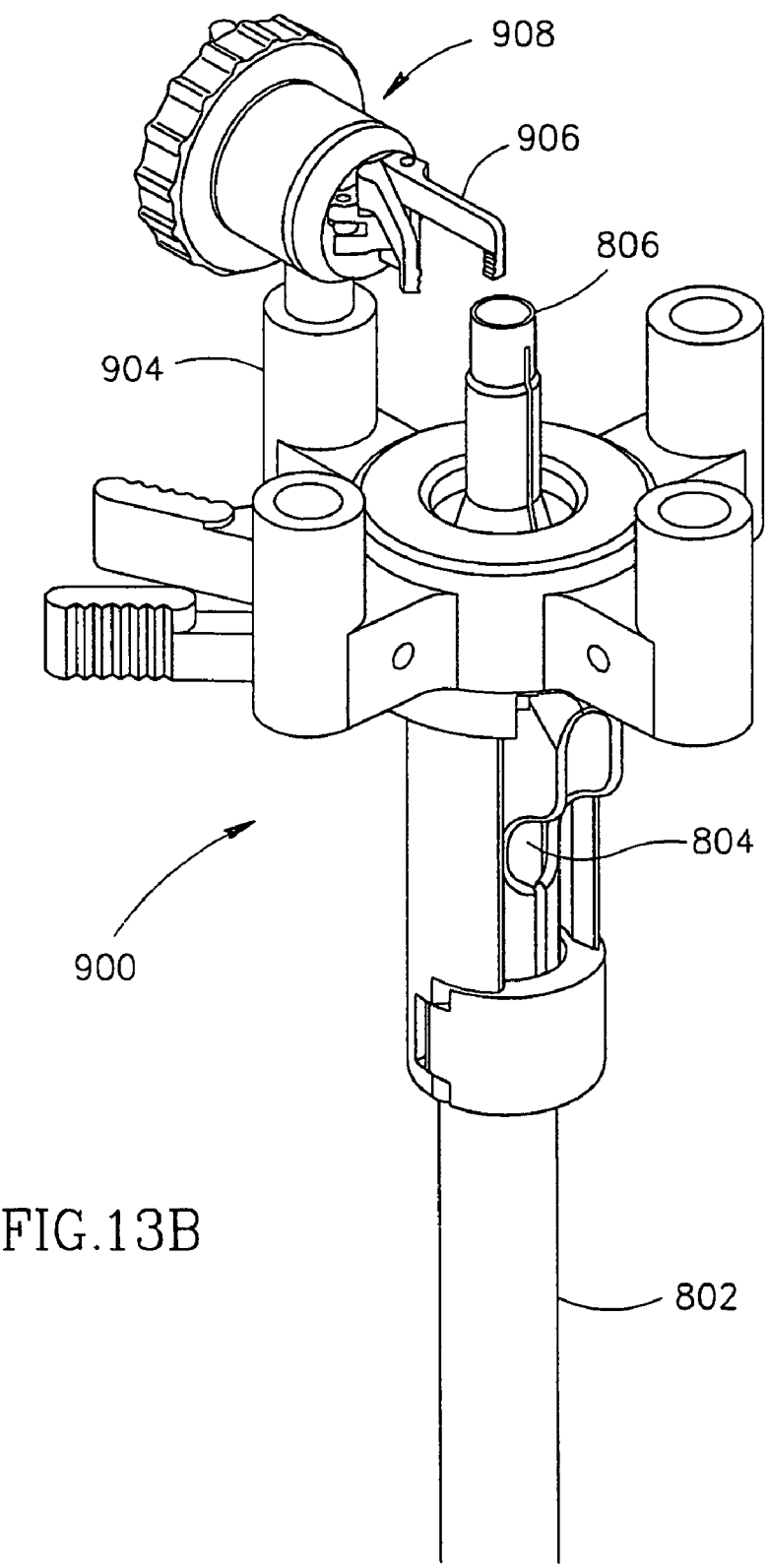

In FIG. 13B, tool 802 is provided in shaft 902. A graft is provided through opening 804 in tool 802 and out of its tip 806. In this figure, a perpendicular, rather than an oblique tip 806 is shown. However, an oblique tip, for example as in FIG. 12, may be used instead, and the motion of forceps 906 is preferably matched to the obliqueness. Depending on the embodiment, an anastomosis connector (not shown) may already be mounted on tip 806, such that the vein everted over it.

Figure 13C:
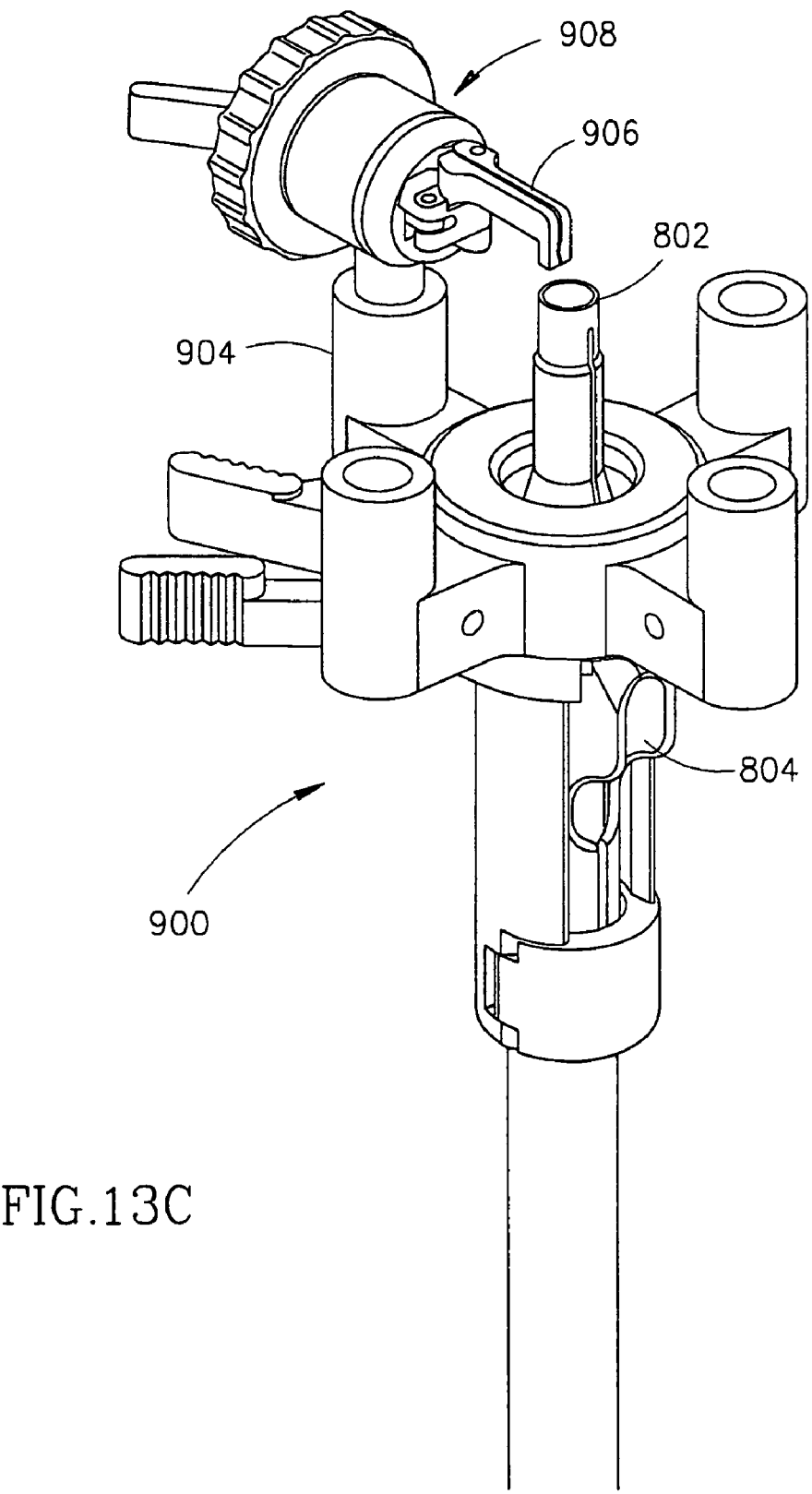

In FIG. 13C, forceps 906 is brought over the tip of graft 132 and closed. It is noted that four pairs of forceps are thus closed on different parts of the graft tip.

Figure 13D:
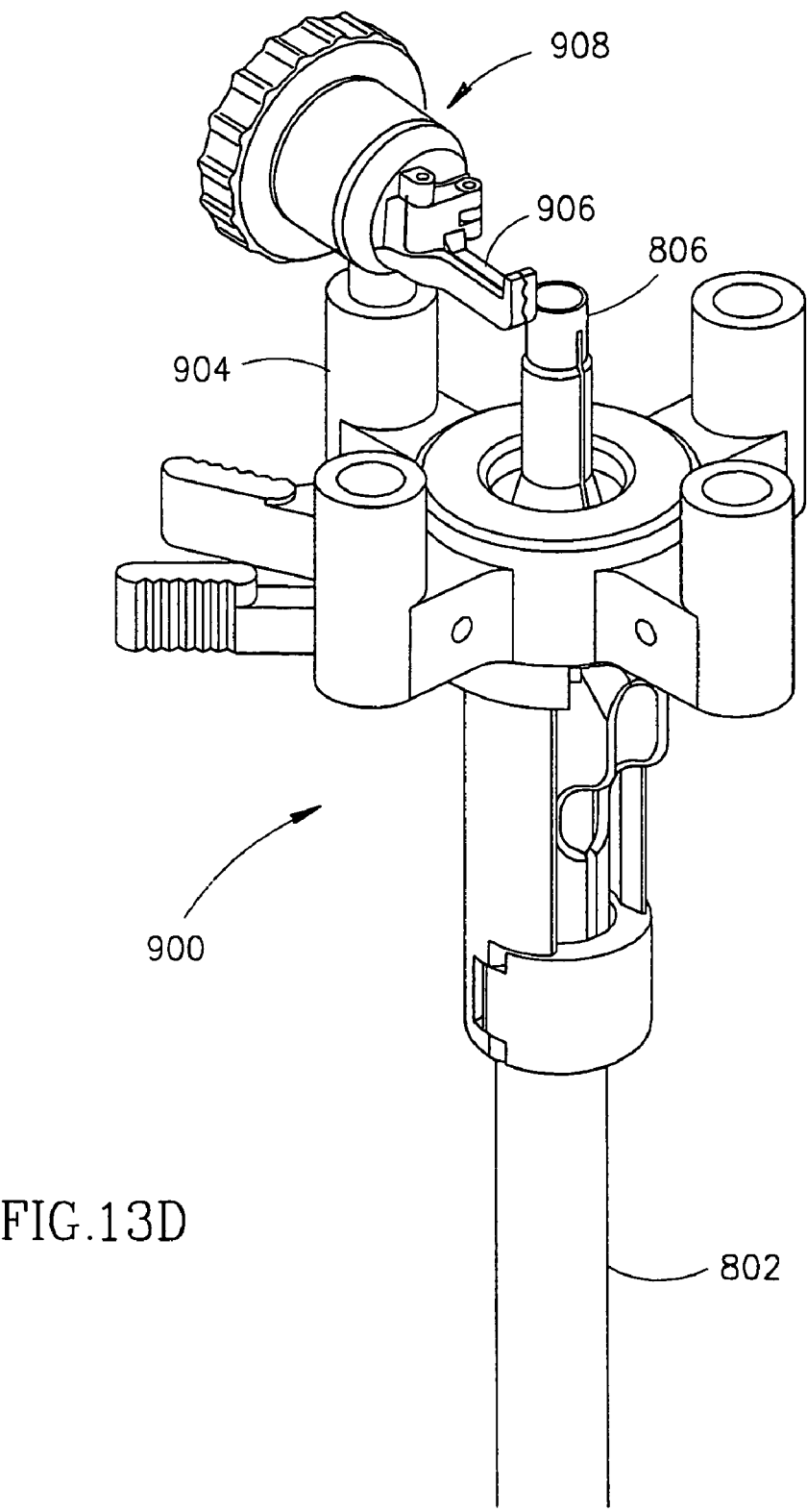

In FIG. 13D, all four forceps are rotated using their mechanism 908, so that the graft is everted. Preferably, all the forceps are rotated simultaneously, alternatively, they are rotated in series. Many mechanism can be used to effect the simultaneous rotation.

Figure 13E:
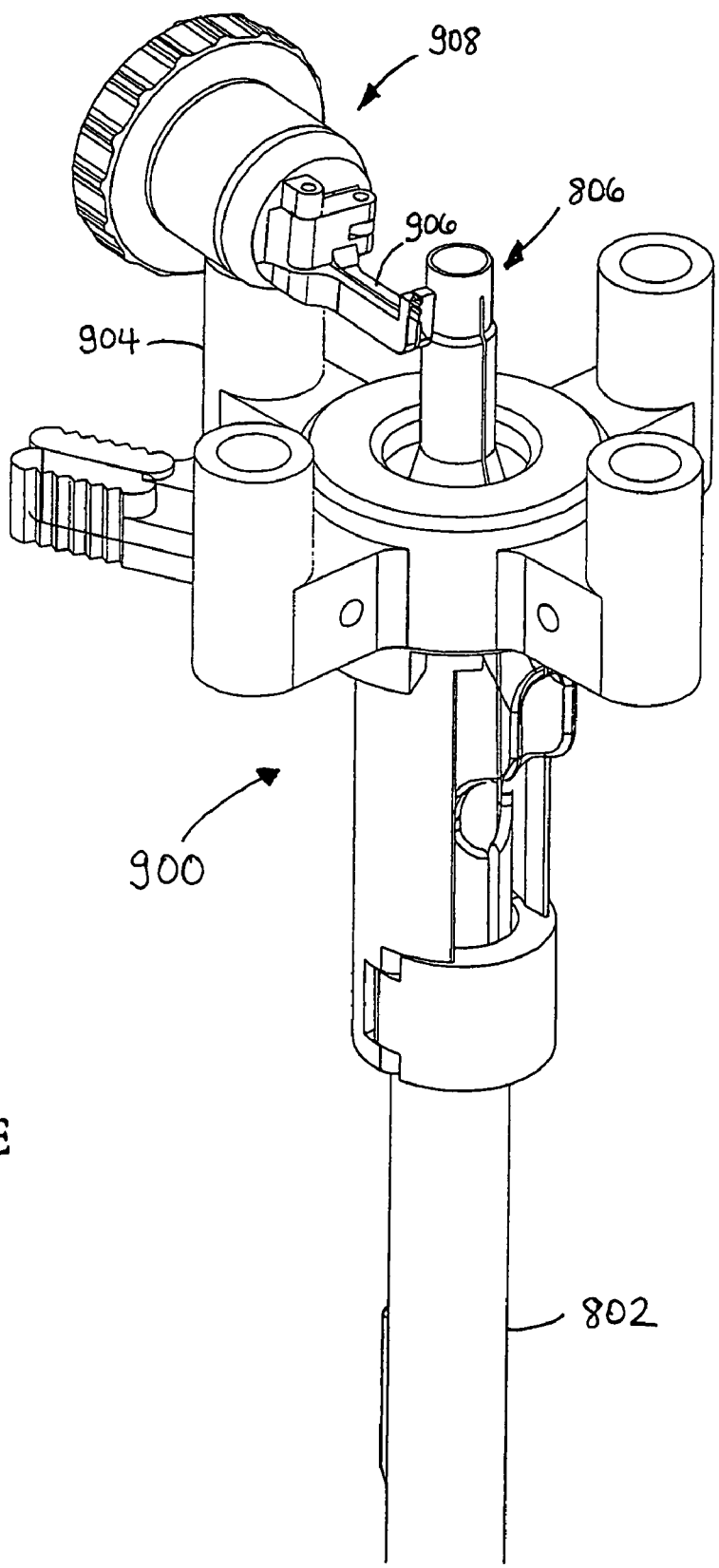

In FIG. 13E, the forceps are pulled down, elongating the eversion length. Optionally, each forceps pulls down a different amount, thereby forming an oblique eversion. Optionally tip 806 has an oblique end, to support the oblique eversion. It is noted that many types of joint mechanisms can be used to effect the rotation and pulling down of the forceps tips.

Figure 13F:
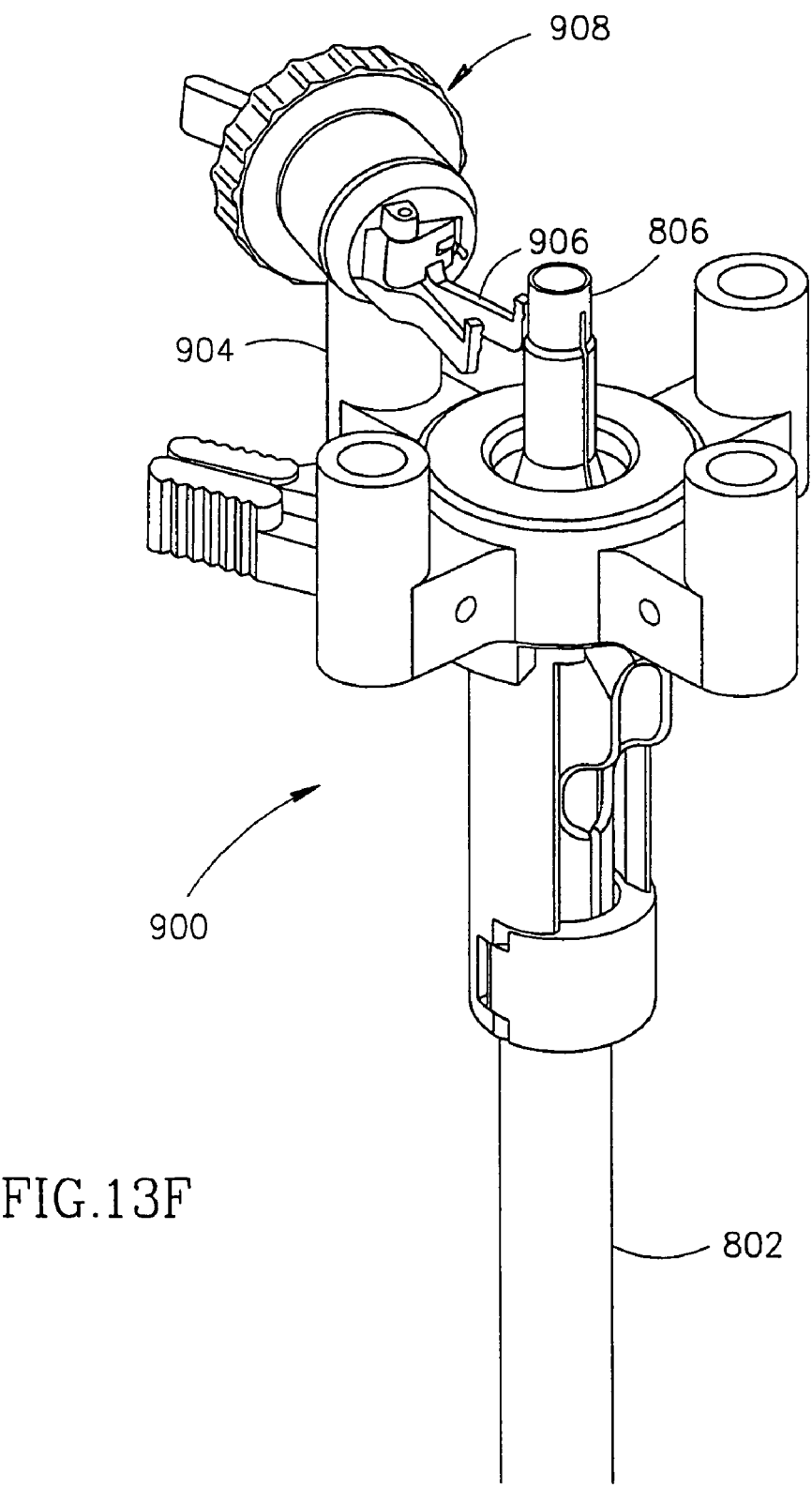

In FIG. 13F, the forceps are opened, releasing the graft and allowing tool 802 to be removed and inserted into handle 800 (if it is not already so inserted.

The inventors have discovered that when a vein is everted obliquely, that is with the everted part having different lengths along the circumference of the eversion, the everted vein tends to bend after a while, in an attempt to release the strain caused by the uneven eversion. In a preferred embodiment of the invention, this mechanism is utilized when forming an eversion, even using a non-oblique anastomosis device, with the result that the graft curves after the anastomosis is completed.

Figure 14:
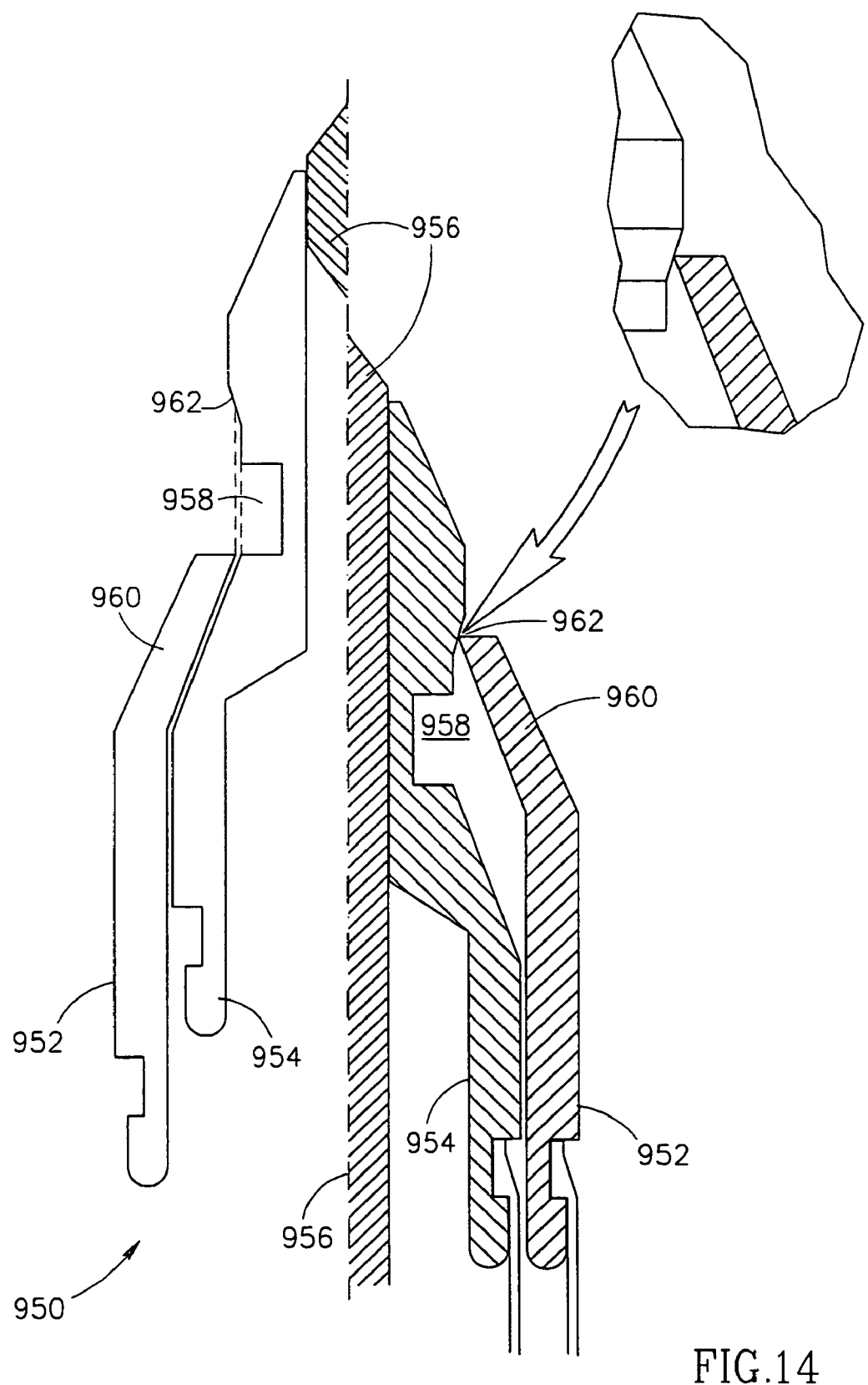
FIG. 14 illustrates a tip of a hole-punching tool, in accordance with a preferred embodiment of the invention.

FIG. 14 illustrates a tip of a hole-punching tool 950, in accordance with a preferred embodiment of the invention. The side of the figure to the left of the axis shows the tip prior to hole punching and the side of the figure to the right of the axis shows the tip after the punching is completed.

Punch 950 comprises an anvil 954 and an outer cutting tube 952. Preferably, a sharp inner tip 956 is used to form an initial hole in vessel 130 and then tip 956 is retracted. After forming the hole anvil 954 is advanced until vessel 130 is engaged by a depression 958 in anvil 954. Depression 958 preferably has an inclined side 962. Cutting tube 952 has a forward portion having a reduced inner diameter that is smaller than the outer diameter of the sides of depression 958. Thus, when cutting tube 952 is advanced, vessel 130 is cut between inclined side 962 and the tip of cutting tube 960. A benefit of this design is the relative laxity of tolerances, as long as the inner diameter of cutting tube 960 matches a diameter of some point of slope 962.

Punch mechanism 950 can be used for both straight and oblique cuts, by varying the location and/or slope 962 of depression 958.

In a typical complete bypass procedure, for the heart, a graft is attached to an aorta and then to a coronary vessel. A similar procedure may be used in other blood vessels, for example the femoral artery. A punch mechanism 950 can be used for both blood vessels. The graft may be, for example, a vein or artery from the same or a different patient. Alternatively, a xenograft or a synthetic graft may be used instead.

The above description has focused on end-to-side anastomosis connectors. However, the above described features can also be applied to side-to-side and end-to-end anastomosis connections and connectors, for example replacing bending spikes with single or double pivot bending spikes. Additionally, the above described spike and ring segment designs may also be applied to hole closure devices, that radially contract and seal a hole formed in a blood vessel. Such devices may include only "forward" spikes, to engage the blood vessel, at its side or at its end.

It will be appreciated that the above described methods of vascular surgery may be varied in many ways, including, changing the order of steps, which steps are performed inside the body and which outside, the order of making the anastomosis connections, the order of steps inside each anastomosis, the exact materials used for the anastomotic connectors and/or which vessel is a "side" side and which vessel (or graft) is an "end" side of an end-to-side anastomosis. Further, in the mechanical embodiments, the location of various elements may be switched, without exceeding the sprit of the disclosure, for example, switching the anvil for the cutting edge in the hole-punching devices and switching the moving elements for non-moving elements where relative motion is required. In addition, a multiplicity of various features, both of method and of devices have been described. It should be appreciated that different features may be combined in different ways. In particular, not all the features shown above in a particular embodiment are necessary in every similar preferred embodiment of the invention. Further, combinations of the above features are also considered to be within the scope of some preferred embodiments of the invention. In addition, some of the features of the invention described herein may be adapted for use with prior art devices, in accordance with other preferred embodiments of the invention. The particular geometric forms used to illustrate the invention should not be considered limiting the invention in its broadest aspect to only those forms, for example, where a circular lumen is shown, in other embodiments an oval lumen may be used.

Also within the scope of the invention are surgical kits which include sets of medical devices suitable for making a single or a small number of anastomosis connections. Measurements are provided to serve only as exemplary measurements for particular cases, the exact measurements applied will vary depending on the application. When used in the following claims, the terms "comprises", "comprising", "includes", "including" or the like means "including but not limited to".

It will be appreciated by a person skilled in the art that the present invention is not limited by what has thus far been described. Rather, the scope of the present invention is limited only by the following claims.

What is claimed is:

1. An anastomosis connector; comprising:
    a plurality of ring segments, together defining a radially expandable ring-like shape having a lumen;
    at least one pivot bar coupled to at least one of said ring segments; and
    at least one spike mounted on said pivot bar and rotatable around said pivot bar,
    wherein radial deformation of said ring-like shape does not substantially directly affect said spike rotational position.

2. A connector according to claim 1, wherein rotation of the pivot bar is mechanically decoupled from radial deformation of ring-like shape.

3. A connector according to claim 2, wherein said at least one pivot bar comprises at least two pivot bars, wherein said at least one spike is mounted on a first one of said pivot bars and said first pivot bar is mounted on the other pivot bar.

4. A connector according to claim 1, wherein said at least one spike is pointed towards said ring-like shape.

5. A connector according to claim 1, wherein said at least one spike is pointed away from said ring-like shape.

6. A connector according to claim 1, wherein said at least one spike comprises at least two spikes, each mounted on a separate pivot bar, wherein said spikes point in opposite directions along an axis of said connector.

7. A connector according to claim 1, wherein said connector is designed such that said at least one spike remains outside of a side vessel in an end-to-side anastomosis.

8. A connector according to claim 1, wherein said connector is designed such that said at least one spike enters a side vessel in an end-to-side anastomosis.

9. A connector according to claim 1, wherein said pivot bar is comprised in a spike element.

10. A connector according to claim 9, wherein said spike element comprises two opposing spikes.

11. A connector according to claim 9, wherein said spike element interconnects two adjacent ring segments.

12. A connector according to claim 9, wherein said spike element is attached to only a single ring element.

13. A connector according to claim 1, wherein said at least one spike has a tip adapted to penetrate a blood vessel.

14. A connector according to claim 1, wherein said at least one spike has a tip adapted to lay against a blood vessel without penetrating it.

15. A connector according to claim 1, wherein said connector is heat-treated to have said at least one spike perpendicular to said ring.

16. A connector according to claim 1, wherein said connector is heat-treated to have said at least one spike parallel to said ring.

17. A connector according to claim 1, wherein said connector is heat-treated to have said at least one spike bend.

18. A connector according to claim 1, wherein said connector is heat-treated such that said at least one spike does not bend.

19. A connector according to claim 1, wherein said connector is heat-treated such that said pivot bar is twisted.

20. A connector according to claim 1, wherein said connector is heat-treated such that said pivot bar is not twisted.

21. A connector according to claim 1, wherein said pivot bar is within an axial extent of said ring-like shape.

22. A connector according to claim 21, wherein said pivot bar is substantially centered relative to said ring like shape.

23. A connector according to claim 1, wherein said pivot bar is outside an axial extent of said ring-like shape.

24. A connector according to claim 1, wherein said pivot bar is comprised in a pivot mechanism.

25. A connector according to claim 24, wherein said pivot mechanism is directly mounted onto at least one of said ring elements.

26. A connector according to claim 24, wherein said pivot mechanism is coupled via a single extension to at least one of said ring elements.

27. A connector according to claim 24, wherein said pivot mechanism is coupled via at least two extensions to at least one of said ring elements.

28. A connector according to claim 24, wherein said pivot bar is coupled to said pivot mechanism via a hinge at each end of said pivot bar.

29. A connector according to claim 28, wherein said hinge comprises a thickening of said mechanism relative to said pivot bar.

30. A connector according to claim 24, wherein said connector comprises a plurality of alternating ring segments and pivot bar mechanism and wherein said pivot bar mechanisms are axially staggered, to allow a greater radial compression of said ring-like shape.

31. A connector according to claim 1, wherein said pivot bar is straight.

32. A connector according to claim 1, wherein said pivot bar is piece-wise straight.

33. A connector according to claim 1, wherein said pivot bar is curved.

34. A connector according to claim 1, wherein said connector is packaged.

35. A connector according to claim 34, wherein said packaging indicates a particular vessel type for said connector and for which said connector is adapted.

36. A connector according to claim 35, wherein said vessel type comprises a femoral artery.

37. A connector according to claim 35, wherein said vessel type comprises an aorta.

38. A connector according to claim 34, wherein said packaging indicates a particular vessel size for said connector and for which said connector is adapted.

39. A connector according to claim 34, wherein said packaging indicates a particular vessel wall thickness for said connector and for which said connector is adapted.

40. A connector according to claim 39, wherein said ring-like shape has an axial extent smaller than said wall thickness.

41. A connector according to claim 34, wherein said packaging indicates a particular connection geometry for said connector and for which said connector is adapted.

42. A connector according to claim 41, wherein said geometry is a side-to-end geometry.

43. A connector according to claim 34, wherein said packaging indicates a particular oblique angle geometry for said connector and for which said connector is adapted.

44. A connector according to claim 1, wherein said at least one spike is cut out of an opposing spike of said connector.

45. A connector according to claim 1, wherein at least one of said ring segments comprises a plurality of axially spaced elements.

46. A connector according to claim 45, wherein said plurality of elements comprises at least three elements.

47. A connector according to claim 45, wherein said plurality of elements comprises at least four elements.

48. A connector according to claim 45, wherein said plurality of elements comprises at least five elements.

49. A connector according to claim 45, wherein all of said plurality of elements have a same geometry.

50. A connector according to claim 45, wherein at least two of said plurality of elements have mirrored geometries.

51. A connector according to claim 45, wherein at least one of said plurality of elements has a single curve geometry.

52. A connector according to claim 45, wherein at least one of said plurality of elements has a dual curve geometry.

53. A connector according to claim 45, wherein at least one of said plurality of elements has at least three curves defined thereby.

54. A connector according to claim 45, wherein at least one of said plurality of elements has a varying width.

55. A connector according to claim 45, wherein all of said plurality of elements have a constant width.

56. A connector according to claim 45, comprising a strain dissipation element at a point of connection of at least one of said elements and a spike element to which said ring segment is attached.

57. A connector according to claim 56, wherein said strain dissipation element comprises a thickening of said axially spaced element.

58. A connector according to claim 57, wherein said thickening defines an aperture.

59. A method of everting a blood vessel, comprising:
  engaging a tip of said vessel at a plurality of points around its circumference;
  inverting said tip by inverting said engaged points; and
  pulling said inverted points towards a distal end of said blood vessel.

60. A method according to claim 59, wherein said plurality comprises at least four points.

61. A method according to claim 59, wherein said engaging comprises engaging using forceps and wherein said inverting comprises rotating said forceps.

62. A method according to any one of claims 59–61, wherein said points are inverted simultaneously.

63. A method according to any one of claims 59–61, wherein said pulling comprises pulling different ones of said points different amounts.

64. Apparatus for graft eversion of a graft over a shaft having a tip, comprising:
  a handle for engaging said shaft;
  a plurality of forceps arranged to engage a tip of said graft where it protrudes form said shaft; and
  a plurality of joints, each one associated with one of said forceps, for rotating said forceps pulling a tip of each of said forceps axially along said shaft.

65. A method of measuring a graft size, comprising:
  mounting a tip of said graft on two extensions, one extension coupled to a spring and one extension coupled to a handle;
  manipulating said handle such that said extensions separate;
  reading a measurement on a scale coupled to said spring; and
  selecting an anastomosis connector responsive to said read measurement.

66. A method according to claim 65, comprising further manipulating said handle to stretch said graft tip.

67. A hole puncher, comprising:
  a sharp tip for forming a puncture in a blood vessel;
  a shaft having a varying diameter and having a depression formed therein for engaging a wall of said blood vessel, said diameter substantially matching a diameter of said tip at one end of the shaft, said diameter increasing away from said tip for a first distance and said diameter then defining a slope of diminishing diameter towards said depression; and
  an outer tube mounted on said shaft and having an end, said outer tube having an inner diameter of said end that is in a range of diameters defined by said slope of diminishing diameters.

68. A puncher according to claim 67, wherein said end of said outer tube has a smaller outer diameter that a more proximal portion of said outer tube.

69. A puncher according to claim 67 or claim 68, wherein said diminishing diameter slope is obliquely arrange around said shaft.

70. A method of forming an oblique anastomosis connector, comprising:
  providing a non-oblique anastomosis connector;
  mounting said connector in a restraint;
  manipulating said restraints to deform said connector to a desired degree of obliqueness; and
  heat-treating said connector after said manipulation, to maintain said distortion.

71. A method according to claim 70, comprising heat-treating said connector prior to said mounting, to train a deformation of a spike portion of said connector.

72. A side mounted delivery system, comprising:
  a handle including an opening in its side;
  a graft delivery tool adapted to fit through said opening; and
  a groove and projection mechanism slidably interconnecting said tool and said handle.

73. A system according to claim 72, comprising a snap-lock mechanism for axially fixing said handle relative to said tool.

* * * * *